(12) United States Patent
Baum et al.

(10) Patent No.: US 6,599,253 B1
(45) Date of Patent: Jul. 29, 2003

(54) NON-INVASIVE, MINIATURE, BREATH MONITORING APPARATUS

(75) Inventors: Marc M. Baum, Pasadena, CA (US); Harry C. Lord, Pasadena, CA (US)

(73) Assignee: Oak Crest Institute of Science, Pasadena, CA (US)

( * ) Notice: Subject to any disclaimer, the term of this patent is extended or adjusted under 35 U.S.C. 154(b) by 44 days.

(21) Appl. No.: 09/891,106

(22) Filed: Jun. 25, 2001

(51) Int. Cl.$^7$ .............................. A61B 5/08; G01J 3/40
(52) U.S. Cl. ...................................... 600/532; 356/303
(58) Field of Search .................................. 600/528, 532; 73/23.3; 422/84; 356/302, 303, 319, 326

(56) References Cited

U.S. PATENT DOCUMENTS

| | | | | |
|---|---|---|---|---|
| 4,648,396 A | * | 3/1987 | Raemer ................... | 128/204.22 |
| 4,914,719 A | * | 4/1990 | Conlon et al. .......... | 250/339.13 |
| 5,046,018 A | * | 9/1991 | Flewelling et al. ......... | 600/532 |
| 5,231,591 A | * | 7/1993 | Flewelling et al. ......... | 600/532 |
| 5,425,374 A | * | 6/1995 | Ueda et al. .................... | 422/84 |
| 6,186,958 B1 | * | 2/2001 | Katzman et al. ............. | 128/898 |

* cited by examiner

Primary Examiner—Edward K. Look
Assistant Examiner—John K Fristoe, Jr.
(74) Attorney, Agent, or Firm—David O'Reilly

(57) ABSTRACT

A rugged, miniature, spectroscopic gas analyzer apparatus for rapid, non-invasive, multi-component breath monitoring and analysis and subsequent determination of Q or other medical diagnostic applications. The system is comprised of one or more IR emitters focussed by optical elements through a low volume sample cell receiving a sample input of a patient's breath for analysis. The patient either at rest or during exercise, inhales $C_2H_2$—$SF_6$ mixtures (balance of oxygen and nitrogen) which is subsequently monitored upon exhalation for $CO_2$, $H_2O$, $C_2H_2$, and $SF_6$ which can be employed to determine Q directly and accurately. Measurements are performed in real-time or via post-processing of stored original data. Due to its small size, ruggedness, and low power consumption, the monitor can conveniently be employed in the field or data can also be retrieved remotely using telemetry. The miniature analyzer operates on the principle of infrared absorption spectroscopy and allows very precise concentration measurements of the analytes of interest, without any bias or interference from other matrix components.

42 Claims, 15 Drawing Sheets

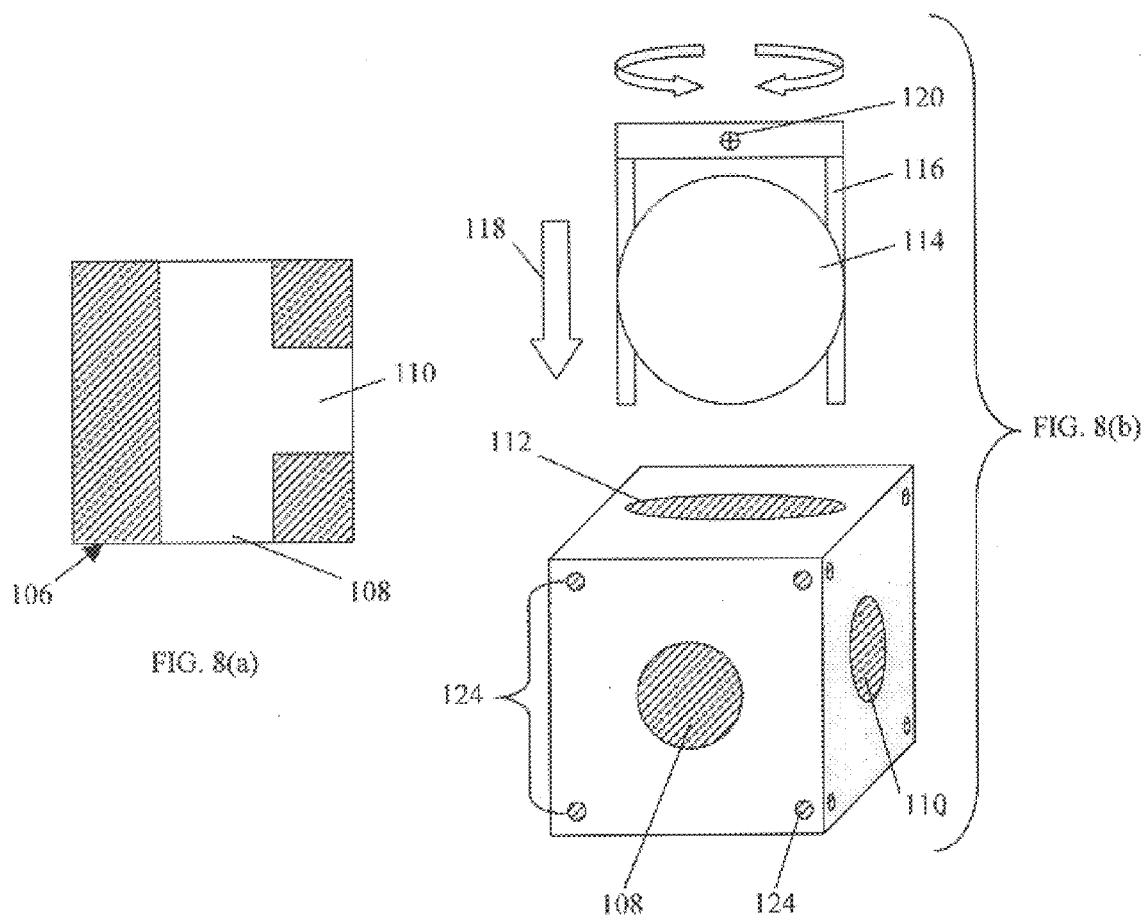
FIG. 8(a)
FIG. 8(b)
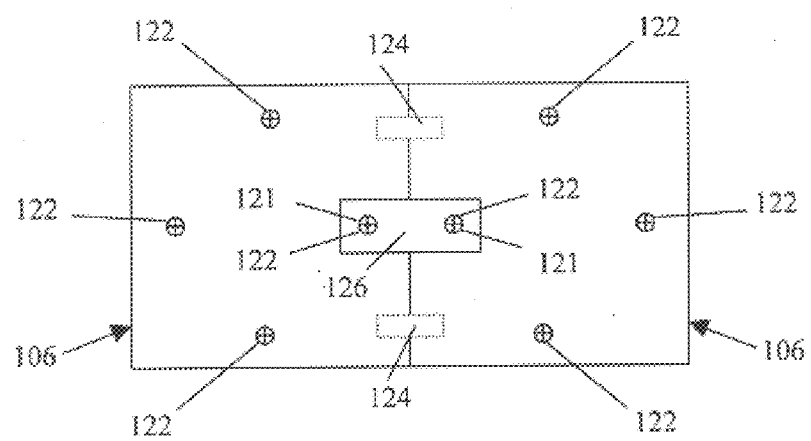
FIG. 8(c)

NON-INVASIVE, MINIATURE, BREATH MONITORING APPARATUS

BACKGROUND OF THE INVENTION

1. Field of the Invention

This invention relates to a breath monitoring apparatus for diagnostic purposes and more particularly relates to a miniature spectroscopic gas analyzer for patient breath analysis to determine cardiac output (Q).

2. Background Information

The determination of Q—the amount of blood pumped by the heart per minute—at rest or during exercise is a powerful diagnostic tool for assessing patient health. Currently, the state of diagnostic technology is hospital and research-center based and features expensive, sensitive equipment.

A series of invasive and non-invasive techniques have been developed for Q monitoring during rest and submaximal exercise. The "gold" standard generally is considered to be the dye-dilution method, with thermodilution a close second. Both methods are invasive and measure Q directly. Noninvasive techniques for Q monitoring encompass four principal approaches: 1) foreign gas rebreathing (e.g., acetylene or nitrous oxide analysis in breath), 2) indirect Fick (e.g., carbon dioxide analysis in breath), 3) transthoracic electrical bioimpedance, and 4) esophageal continuous-wave Doppler ultrasonography. These prior art methods are described below, along with their strengths and weaknesses.

Thermodilution (TD) is the traditional method for continuous and semicontinuous Q determination and many publications describe such a method. (Zollner, C. et al, Crit. Care Med. 1999, 27, 293–298; and Zollner, C. et al, J. Cardiothorac. Vasc. Anesth. 2000, 14, 125–129.) Also, numerous patents describing TD apparatus and accessories have been issued. Patents issued include U.S. Pat. No. 4,217,910, issued Aug. 19, 1980 to Khalil, H. H. for Internal jugular and left ventricular thermodilution catheter; U.S. Pat. No. 4,236,527, issued Dec. 2, 1980 to Newbower, R. S. et al for a Q detection by multiple frequency thermodilution and U.S. Pat. No. 4,819,655, issued Apr. 11, 1989 to Webler, W. E. for an Injectateless thermal Q determination method and apparatus.

However, this technique has significant drawbacks, primarily resulting from its invasive nature. A catheter needs to be inserted into the pulmonary artery and manual injection of fluid into the blood typically is required. Due to the serious nature of these interventions, the technique is usually restricted to monitoring hospitalized critically ill patients. Additionally, the response time of thermodilution monitors is too slow for the immediate detection of acute changes in Q and some clinical conditions, such as the rapid infusion of cold solutions, can interfere with the continuous Q measurement (Haller, M.; Zollner, C.; Briegel, J.; Forst, H., Crit. Care Med. 1995, 23, 860–866).

Non-Invasive methods of measuring Q include: Transthoracic electrical bioimpedance (TEB) monitors are non-invasive alternatives to TD but require the use of an endotracheal tube, which limits the technique's practicality. (Vohra, A. et al, Br. J. Anaesth. 1991, 67, 64–68; Tibballs, J. et al, Anaesth. Intensive Care 1992, 20, 326–331; and Wallace, A. W. et al, Anesthesiology 2000, 92, 178–189). A number of patents describing the TEB technique have been issued (e.g., U.S. Pat. No. 5,423,326, issued Jun. 13, 1995, to Wang, X. et al, for an Apparatus and method for measuring Q and U.S. Pat. No. 5,469,859, issued Nov. 28, 1995 to Tsoglin, A. et al for a Non-invasive method and device for collecting measurements representing body activity and determining cardiorespiratory parameters of the human body based upon the measurements collected.).

Esophageal continuous-wave Doppler ultrasonography (ECO) has also emerged as a non-invasive method for Q monitoring (Pierpont, G. L. et al, J. Cardiovasc. Technol. 1990, 9, 31–34; Schiller, N. B., Anesthesiology 1991, 74, 9–14; and Webster, J. H. H. et al, European Journal of Vascular Surgery 1992, 6, 467–470). ECO has the advantage of being a non-invasive technique and has been recommended over thoracic electrical bio-impedance and thermodilution for field monitoring of seriously injured soldiers. (World, M. J. QJM-Mon. J. Assoc. Physicians 1996, 89, 457–462)

A number of Q monitors using the ECO technique have been patented. (e.g., U.S. Pat. No. 4,676,253, issued Jun. 30, 1987 to Baudino, M. D. for a Q monitor; U.S. Pat. No. 4,676,253, issued Jun. 30, 1987, to Newman, W. et al, for a Method and apparatus for non-invasive determination of Q; and U.S. Pat. No. 4,671,295, issued 1987, to Abrams, J. H. et al, for a Method for measuring Q.

A serious limitation of both the TEB and ECO methods is their inability to be employed during exercise due to excessive noise. A method of monitoring Q by computing blood pressure waveforms with fuzzy logic algorithms has also been disclosed recently, but has not been shown to be reliable or accurate especially when the subject is exercising. (U.S. Pat. No. 6,007,491, issued Dec. 28, 1999 to Ling, J. et al, for a Q monitor using fuzzy logic blood pressure analysis.)

Metabolic monitors commonly have been used to measure oxygen ($O_2$) consumption and/or carbon dioxide ($CO_2$) production to subsequently calculate Q. Such monitors are described by Zenger, M. R. et al, Am. J. Cardiol. 1993, 71, 105–109; Sasse, S. A. et al, Crit. Care Med. 1994, 22, 86–95; and Wippermann, C. F. et al, Intensive Care Med. 1996, 22, 467–471. Some of these devices have been patented (e.g., U.S. Pat. No. 5,836,300, issued Nov. 17, 1998; to Mault, J. R. for a Metabolic gas exchange and non-invasive Q monitor; and U.S. Pat. No. 5,971,934, issued Oct. 26, 1999 to Scherer, P. W. et al for a Non-invasive method for determining Q). However, the $CO_2$ re-breathing method relies on a number of tenuous assumptions and is difficult to use during heavy exercise.

Non-invasive diagnostic methods for measuring Q using soluble gas uptake by the lungs also have existed for many years. Acetylene ($C_2H_2$) has been useful in such techniques, because its appropriate blood to gas partition coefficient usually lies in the range of 0.7–0.9 and is generally the preferred method for non-invasive Q monitoring. (Kennedy, R. R. et al Br. J. Anaesth. 1993, 71, 398–402 and Rosenthal, M. et al, Eur. Resp. J. 1997, 10, 2586–2590). $C_2H_2$-helium re-breathing techniques are based on the principle that $C_2H_2$, but not helium (He), diffuses from the alveoli to the pulmonary capillaries so that the rate of $C_2H_2$ decrease in the alveolar space depends on pulmonary blood flow. The traditional approach has been to measure $C_2H_2$ uptake during rebreathing from a closed system (Kallay, M. C. et al, Circulation 1985, 72, 188–188 and Crapo, R. O. et al, Am. Rev. Respir. Dis. 1986, 133, A65-A65.) However a non-rebreathing open-circuit steady-state method has also been reported. (Barker, R. C. et al, J. Appl. Physiol. 1999, 87, 1506–1512)

Both require rapid gas analyzers, especially if measurements are to be made at high breathing frequencies during exercise. An insoluble gas, such as He or sulfur hexafluoride ($SF_6$) is required to determine the gas volume in the system and also as an indication when gas mixing is achieved. Carbon dioxide concentrations are also needed to convert measured minute ventilation to alveolar ventilation. It is alveolar and not minute ventilation that is used in the formula to determine Q.

The current instrument of choice for measuring $C_2H_2$ in breath is the respiratory mass spectrometer (MS). A sample is channeled from the breathing apparatus and introduced into the MS, where it is ionized and detected on a semi-continuous basis. Although this technique is reasonably fast (response times down to 20 msec., but typically 50 msec.), it does have some inherent limitations, including:

a.) Primarily a lab instrument,
b.) High power consumption,
c.) Bulky,
d.) High sensitivity to mechanical vibration and shock,
e.) Complex to use,
f.) Expensive to buy and maintain.

Faster response times are also important as the $C_2H_2$ concentration profile within a single breath is of interest. A portable, robust, non-invasive, low cost alternative to mass spectrometry measuring $C_2H_2$, $CO_2$, and $SF_6$ (or He) with very fast response times thus would be desirable. Portable infrared (IR) spectrometers have been used to monitor $C_2H_2$ but the performance of these instruments is questionable (possibly due to poor control of the sample cell environment and water interferences) and a MS is still required to measure the tracer gas, which is usually He. (Barazanji, K. W. et al, J. Appl. Physiol. 1996, 80, 1258–1262); Additionally, these IR analyzers are very slow (response time 200–300 msec.) and are single gas analyzers (i.e., one unit for each monitored gas, usually CO, $CH_4$, and $C_2H_2$). Hence, metabolic carts equipped with an optional $C_2H_2$ analyzer are not generally effective technically, practically (bulky and intended for lab use only), or economically.

Clemensen et al. employed a multicomponent ($O_2$, $CO_2$, chlorodifluoromethane, and $SF_6$) photoacoustic infrared and paramagnetic (IR/PM) gas analyzer in inert gas-rebreathing and metabolic gas exchange measurements. (Clemensen, P. et al, J. Appl. Physiol. 1994, 76, 2832–2839) The feasibility of replacing a conventional MS by such an instrument in a variety of non-invasive pulmonary gas exchange measurements was investigated for 10 subjects at rest and during submaximal exercise. The IR/PM showed promise, although further modifications to the instrument appeared to be required. This is the only report on the use of a spectroscopic gas analyzer measuring $CO_2$, $SF_6$, and a soluble gas, chlorodifluoromethane (freon 22). However, the system has important practical drawbacks, including cost and very slow response times (250 msec.).

It is one object of the present invention to provide a non-invasive, miniature breath monitoring and analysis device based on the measurement of a plurality of analytes via absorption spectroscopy.

Yet another object of the present invention is to provide a non-invasive breath monitoring and analysis device for measuring Q based on the measurement of acetylene ($C_2H_2$), carbon dioxide ($CO_2$), sulfur hexafluoride ($SF_6$), and water ($H_2O$) via IR absorption spectroscopy.

Still another object of the present invention is to provide a non-invasive, breath monitoring analysis device where one or more gases are replaced by suitable alternatives (e.g., CO or $N_2O$ instead of $C_2H_2$, $CH_4$ instead of $SF_6$).

Still another object of the present invention is to provide a non-invasive, miniature breath monitoring and analysis device that uses existing re-breathing and non-re-breathing protocols and data treatment.

Yet another object of the present invention is to provide a non-invasive, breath monitoring device that can be used with the subject at rest or under exercise; and can be used even under very heavy exercise.

Yet another object of the present invention is to provide a non-invasive, miniature breath monitoring device with an optional oxygen ($O_2$) measurement.

Still another object of the present invention is to provide a non-invasive, miniature breath monitoring device that is low in cost to manufacture, rugged, portable, compact, low-power consumption, easy to maintain, allowing rapid transition from the laboratory to commercialization compared to the re-breathing mass spectrometer.

Still another object of the present invention is to provide a non-invasive, miniature breath monitoring device that does not need liquid nitrogen ($LN_2$) cooling.

Yet another object of the present invention is to provide a breath monitoring analysis device for diagnostic purposes that has physical characteristics that allow the device to be used in the field.

Yet another object of the present invention is to provide a miniature breath monitoring and analysis device that allows data collected to be retrieved remotely by telemetry.

Still another object of the present invention is to provide a non-invasive, miniature breath monitoring analysis device that has fast response time of less than about 50 msec.

Another important object of the present invention is to provide a non-invasive, breath monitoring analysis device that uses low sampling volumes to keep the device compact and portable and with a fast response time.

Yet another object of the present invention is to provide a non-invasive, breath monitoring analysis device that includes a plurality of dedicated detectors—at least one per analyte—to monitor each compound of interest.

Still another object of the present invention is to provide a non-invasive, miniature breath monitoring device that allows analysis to be carried out in parallel, and measures the contents of a single optical sample cell.

Yet another object of the present invention is to provide a non-invasive, breath monitoring device that has a 100% duty cycle without the need for rotating filter wheels, or multiple sensors analyzing the contents of multiple sample cells.

Yet another object of the present invention is to provide a non-invasive breath monitoring device that utilizes one central processing unit (CPU) to manage all measurements.

Still another object of the present invention is to provide a non-invasive, miniature breath monitoring device that utilizes stackable, compact electronics.

Still another object of the present invention is to provide a non-invasive, miniature breath monitoring device that uses one or more fast response time detectors measuring $SF_6$ or other gases, in the far-IR (i.e., $\lambda > 5.5 \mu m$) without the need for $LN_2$ cooling.

Yet another object of the present invention is to provide a non-invasive, miniature breath monitoring device that removes spectral interference by using a gas cell filled with a high-optical depth of water vapor or any other spectral interferents in-line with the sample cell.

Still another object of the present invention is to provide a non-invasive, miniature monitoring device that utilizes an innovative, compact, modular optical design employing a plurality of beamsplitters for any combination of between 3 to 7 measurement channels.

Yet another object of the present invention is to provide a non-invasive breath monitoring device that uses optical fibers to guide the radiation to the measurement channels in lieu of multiple beamsplitters.

Yet another object of the present invention is to provide a non-invasive, miniature breath monitoring device that utilizes sequentially-pulse, multiple sources (e.g., TDL, LED, pulsed incandescent) coupled by optical fibers and one measurement detector.

Yet another object of the present invention is to provide a non-invasive, miniature breath monitoring device in which one embodiment allows for in-situ monitoring directly at the mouthpiece.

Still another object of the present invention is to provide a non-invasive, miniature breath monitoring device that can be easily adapted to monitor a wide range of gases relevant to Q monitoring and other medical applications of breath analysis by replacement of optical filters or sample cells.

BRIEF DESCRIPTION OF THE INVENTION

The purpose of the present invention is to provide a non-invasive, miniature breath monitoring device or system that can be used as an effective medical diagnostic tool. The non-invasive, miniature breath monitoring device system disclosed herein utilizes an analyzer that is unique by virtue of a simultaneous and continuous measurement of $C_2H_2$, $CO_2$, and $SF_6$ in a gaseous matrix in one low-cost, miniature device approximately the size of a shoe box. The analyzer response is linear over full-scale ranges of 1.0–2.0%$_v$ for $C_2H_2$ and $SF_6$; 10%$_v$ for $CO_2$. A full-scale reading of 20% $O_2$ is an optional add-on feature. The analyzer detection limits (2σ) are 2% of full-scale, or better, with a 10–50 msec. response time (10–90%); accuracy is typically ±2% of full-scale, or better. The rapid response time of the analyzer also distinguishes it from other gas analyzes used in the art. Unlike other IR $C_2H_2$ monitors, it does not suffer from cross-interferences, notably from $H_2O$ vapor. The instrument has a low sample volume (preferably less than 1.25 mL) and requires low power input (less than 50 watts during warm up, less than 25 watts during steady state). It is suitable for telemetry and is rugged with very low maintenance requirements.

The miniature breath monitoring device disclosed herein can be used in conjunction with the $C_2H_2$ foreign gas method to determine Q, by the re-breathing and non-rebreathing techniques. The latter is relatively new approach to Q monitoring, which is attractive in exercise studies, especially at altitude, as it avoids unpleasant re-breathing and resulting changes in alveolar $PO_2$ or $PCO_2$ as described in J. Appl. Physiol 1999, 87, 1506–1512 by Barker, R. C. et al.

Because of its compact, miniaturized size, the Q monitoring technology has a number of applications. It can be applied to monitoring hospitalized patients in critical and intensive care as well as in birthing rooms, screening of undeserved civilian communities, particularly in remote locations; rehabilitation exercise programs particularly following surgery; ambulance diagnostics; sports medicine and exercise physiology; screening of soldiers and potentially allowing a number of injured soldiers to be assessed rapidly; high altitude medical research; sustained micro-gravity research; and in animal studies particularly for dogs and horses.

Breath analysis as a non-invasive means of medical diagnostics has been touted for many years but the evolution of suitable instruments has been slow. U.S. Pat. No. 3,951,607 issued Apr. 20, 1976 to Fraser, R. B. for a gas analyzer discloses a chamber for measuring a number of breath components by mass spectrometry. The present invention is not limited in its usefulness to Q monitoring. Other applications include but are not limited to medical diagnostics by breath analysis of the following compounds:

a) carbon monoxide (CO) and a suitable inert reference gas (e.g., $SF_6$ or $CH_4$) for measuring lung volume and diffusing capacity and for evaluation of carboxyhemoglobin. In premature infant breath infected with hyperbilirubinemia, or hemolytic disease, breath analysis can be used as an index by bilirubin production. Statistics on measurement data can help predict whether the neonate is likely to develop potentially dangerous jaundice or not, b) Acetone (1–500 μg $L^{-1}$) for diabetes diagnosis, c) Nitric oxide (NO) (0–100 ppb) for monitoring patients with pneumonia, COPD exacerbation, cystic fibrosis, undergoing CABG, cirrhosis and/or on intravenous nitroglycerin. Also, the therapeutic administration of NO is now common practice in an intensive care environment for catastrophic lung disease, but the NO concentration in exhaled breath is not commonly measured. An analyzer capable of measuring the NO levels in exhaled breath would be useful for controlling the administered levels as well as determining the relationship between the treated disorder and the appropriate NO concentration in inhaled air for therapeutic treatment, d) Hydrogen peroxide for investigating lung oxidative damage, e) Ammonia ($NH_3$), possibly for monitoring liver disease and in metabolic studies (e.g., during exercise).

f) $^{12}CO_2/^{13}CO_2$ for monitoring the administration of $^{13}C$-labeled substances, such as used in screening of patients for glucose utilization, pancreatic function, intestinal bacterial overgrowth, liver function, and *H. pylori* infections of the digestive tract. Non-invasive evaluation of the nutritional status and body composition in pediatric patients also can be achieved by monitoring exhaled $^{13}CO_2$, following bolus administration of $^{13}CO_2$, g) Breath ethane as a biomarker of free radical-mediated lipid peroxidation following reperfusion of the ichemic liver, h) Sulfur compounds for diagnosis of liver dysfunction, i) Anesthetic administration, including nitrous oxide ($N_2O$), j) Toxics (e.g., volatile organic compounds, either speciated or total) for occupational exposure monitoring.

The principal purpose of the invention disclosed herein consists in the quantitative analysis of gas-phase components of breath and the subsequent determination of Q. This measurement is made non-invasively by using novel embodiments of spectroscopic gas sensing technology. The present invention is unique in its optical design and by virtue of the fact that high-speed IR spectrometers are employed to monitor multiple species to determine an accurate measurement of Q. The use of such an approach has not been reported previously to make Q measurements on subjects at rest or during exercise.

With minor adjustments, the instrument is capable of measuring alternative analytes that may be of interest for Q monitoring (e.g., methane and freon 22). The integration of an $O_2$ measurement channel allows the metabolic measurements to be carried out in conjunction with Q monitoring.

Similarly, the instrument has the capability of measuring numerous other gases, such as $NH_3$, CO, $N_2O$, ethanol, acetone, aldehydes, etc. for other biomedical applications, as described above. Substitution of the standard four measurement channels (i e $CO_2$, $H_2O$, $C_2H_2$, and $SF_6$) with any of the above does not necessitate any software modifications and only requires minor hardware modifications (i.e., substitution of the optical filters).

The three principal gases of interest to Q monitoring, $C_2H_2$, $CO_2$, and $SF_6$, all possess unique IR absorption signatures centered at different wavelengths, as shown by FIG. 1. The amount of absorption is directly proportional to gas concentration, as described by the Beer-Lambert law. (Banwell, C. N. *Fundamentals of Molecular Spectroscopy*; 3 ed.; McGraw-Hill: London, 1983) For monitoring Q, a subject typically breathes an atmosphere consisting of $C_2H_2$ (approximately $2\%_v$), $SF_6$ (approximately $2\%_v$), and $O_2$ (20–30%$_v$), balance nitrogen. $CO_2$ is also present in exhaled breath. Therefore, a spectrometer that isolates the spectral window corresponding to the absorption signature of the target gases allows them to be monitored non-invasively and continuously by measuring the amount of radiation passing through the sample. A commonly used approach, known as non-dispersive IR (NDIR) spectroscopy (Hanst, P. L.; Hanst, S. T. *Gas Measurement in the Fundamental Infrared Region*; Sigrist, M. W., Ed.; John Wiley & Sons: New York, Chichester, Brisbane, Toronto, Singapore, 1994; Vol. 127, pp 335–470), relies on narrow bandpass optical filters (NBOFs) to isolate the radiation used to probe the fluid. The wavelength of this radiation is chosen to match that of the analyte's absorption band. While this technique has been widely-used for gas analysis, it has not been applied to Q monitoring in the manner disclosed here. (e.g., U.S. Pat. No. 3,837,744, issued Sep. 24, 1974 to Egan, D. W. et al for Spectrometers, and U.S. Pat. No. 4,632,563, issued Dec. 30, 1986 to Lord, H. C. for Stack Gas Analysis, and U.S. Pat. No. 5,210,702, issued May 11, 1993 to Bishop, G. et al for Apparatus for Remote Analysis of Vehicle Emissions.)

The analyzer of the present invention uses a collimated beam of infrared (IR) radiation projected through a miniature sample cell. The radiation is subsequently analyzed by one or more spectrometers. The extent of signal attenuation as a function of radiation wavelength affords a direct measure of gas concentration and, hence, Q. The instrument uses small (e.g., diameter 12.5 mm) optics and low sample volumes (approximately 1.25 mL) leading to its miniature design.

The IR spectrometers in the analyzer sample at high frequencies (e.g., 2 KHz), yielding valuable Q information within a single breath. Measurements are preferably made in parallel and are automatically synchronized in the electronics. The instrument is calibrated using small samples of certified gas mixtures and is zeroed prior to each Q measurement. The breath analysis monitor is highly stable and insensitive to spectral interferences requiring no reference detector, although one may be included in certain embodiments of the invention.

The signals at the IR spectrometers, in the form of digital counts, are output to a storage device in the analyzer. These are converted to concentration readings and, hence, Q in real-time or by post-processing. Data is accessed/transmitted remotely by a radio modem, making the device useful in field telemetry applications.

The above and other objects, advantages, and novel features of the invention will be more fully understood from the following detailed description and the accompanying drawings, in which:

BRIEF DESCRIPTION OF THE DRAWINGS

FIG. 8(a) is a top view of a beamsplitter optical chamber used in the invention.

FIG. 8(b) illustrates the assembly of the beamsplitter optical chamber used in the invention.

FIG. 8(c) illustrates the connection of multiple beamsplitter optical chambers to insure precise alignment.

DETAILED DESCRIPTION OF THE PREFERRED EMBODIMENTS

Figure 1A:
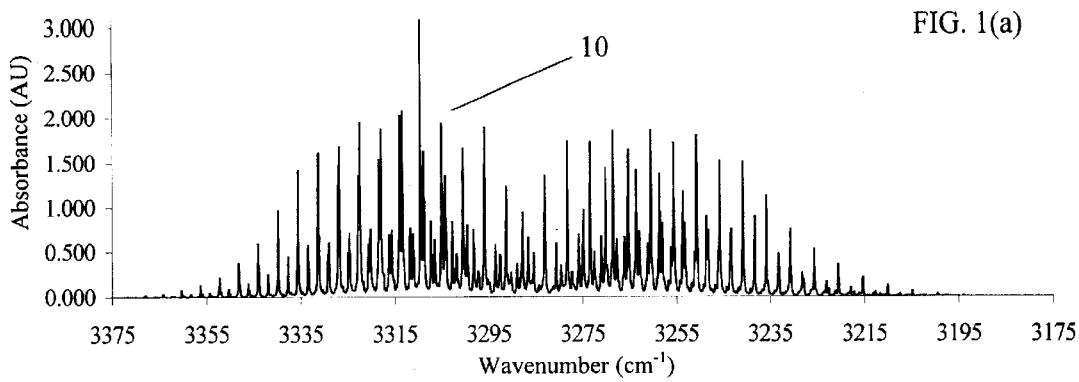
FIGS. 1(a) through 1(d) are stacked IR Spectra of the analytes commonly measured by the invention for Q monitoring (i.e., $C_2H_2$, $CO_2$, $H_2O$, and $SF_6$).
Figure 1B:
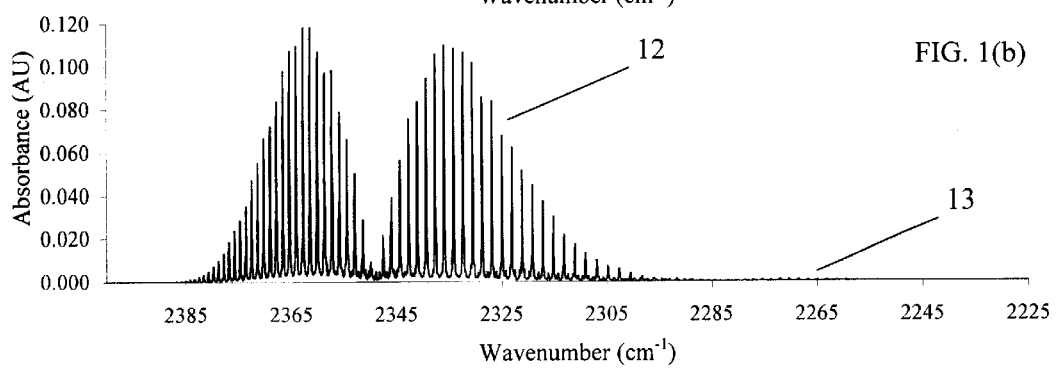
Figure 1C:
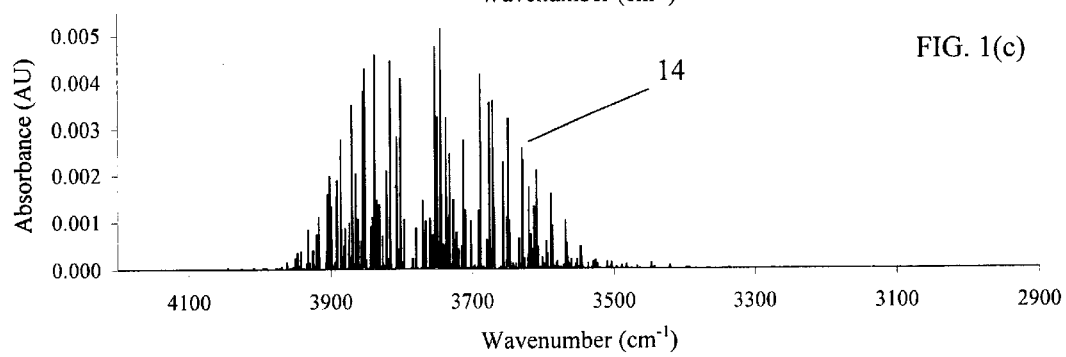
Figure 1D:
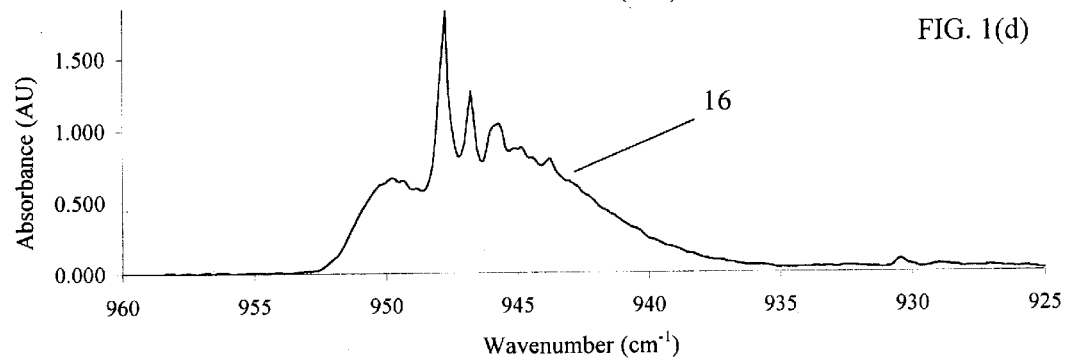

The stacked IR Spectra of analytes commonly measured by the invention disclosed herein are illustrated in the graphs of FIGS. 1(a) through 1(d). FIG. 1(a) illustrates the spectra for acetylene ($C_2H_2$); FIG. 1(b) is the spectra of carbon dioxide ($CO_2$) 12; FIG. 1(c) is the spectra of an analyte of water 14 ($H_2O$); and FIG. 1(d) is a spectra of sulfur hexafluoride ($SF_6$) 16.

Figure 2A:
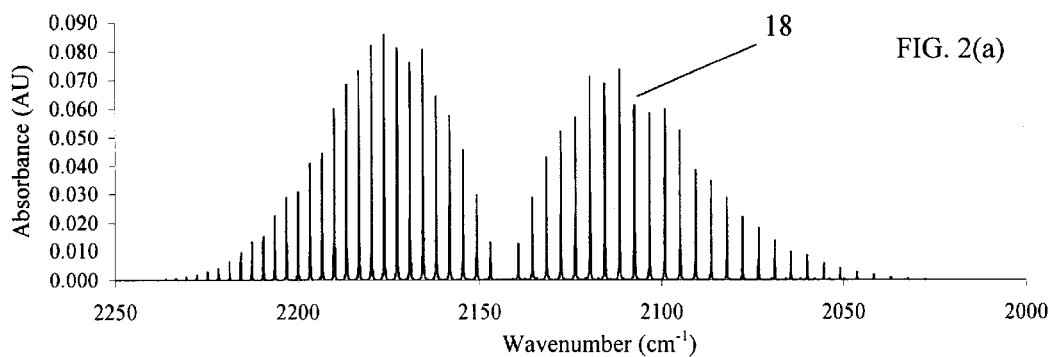
FIGS. 2(a) through 2(b) are graphs illustrating stacked IR spectra of additional analytes of interest to breath analysis that can be measured by the invention (i.e., CO, $N_2O$, $NH_3$, and acetone).
Figure 2B:
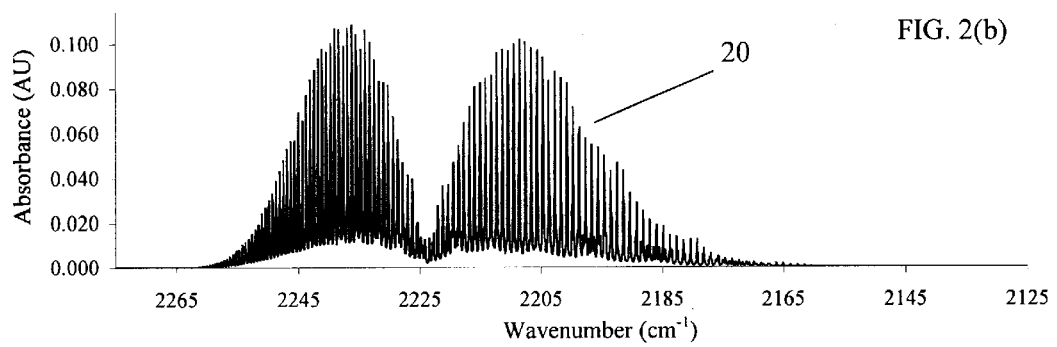
Figure 2C:
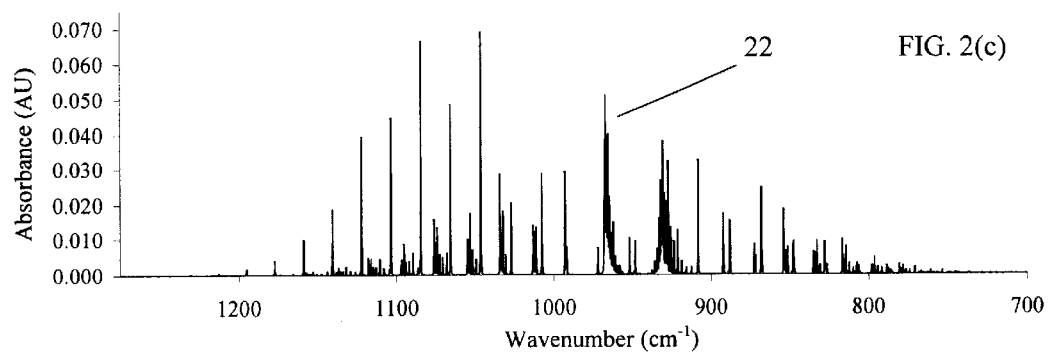
Figure 2D:
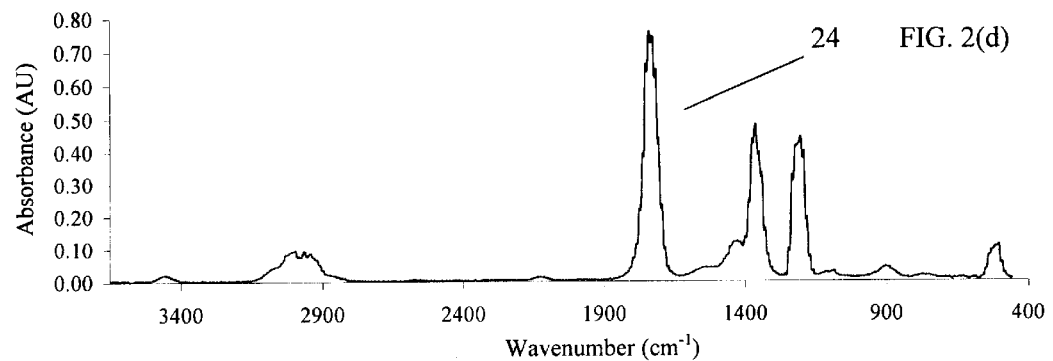

FIGS. 2(a) through 2(d) are graphs of stacked IR spectra of additional analytes of interest to breath analysis that can be measured by the invention disclosed herein. FIG. 2(a) is the spectra of carbon monoxide (CO) 18; FIG. 2(b) is the spectra of nitrous oxide ($N_2O$) 20; FIG. 2(c) is the spectra of ammonia ($NH_3$) 22; FIG. 2(d) is the spectra of acetone 24. Each of the analytes of these spectra can be measured by the analyzer of the present invention.

Figure 3:
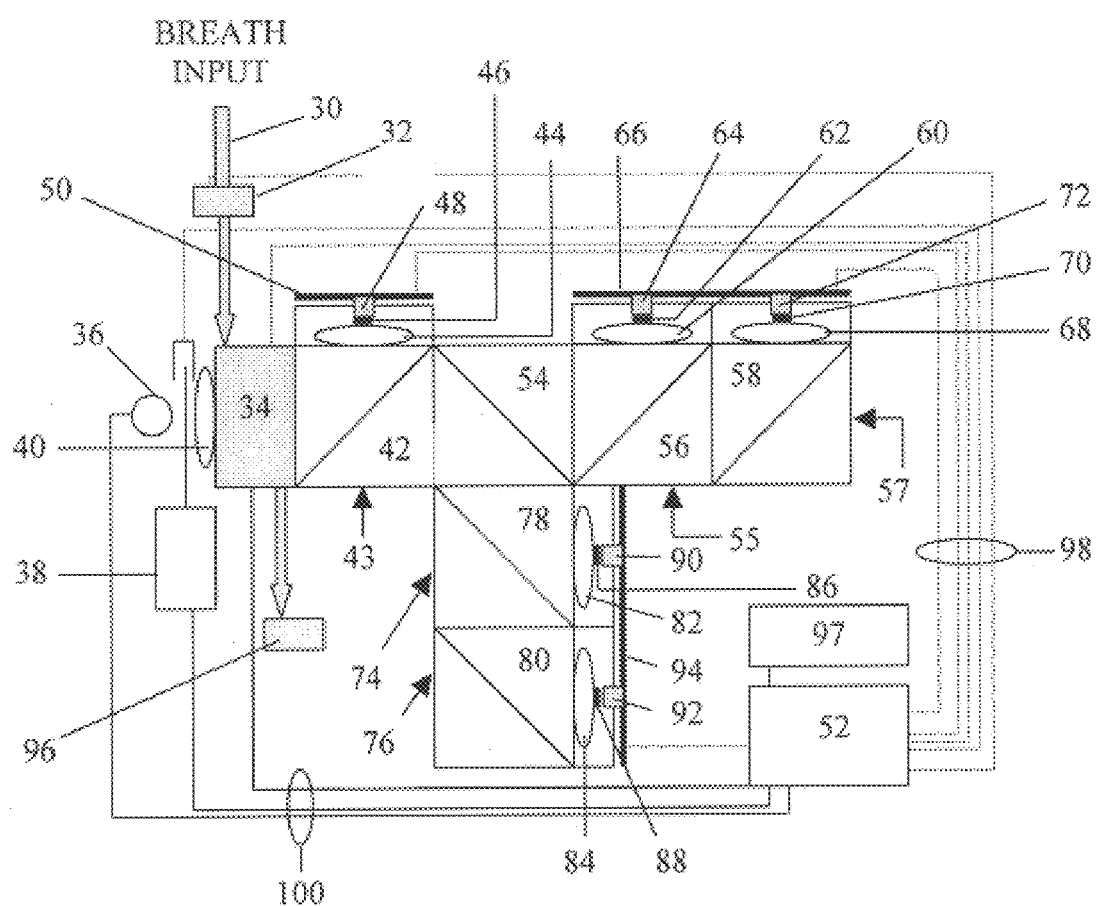
FIG. 3 is a schematic block diagram of a first embodiment of the invention for analyzing a breath sample.

A preferred embodiment of the present invention is illustrated in the schematic block diagram of FIG. 3. The subject or patient breathes into an apparatus that is input through tube 30 and flow rate monitor 32 through sample gas cell 34. Radiation from IR emitter 36 is modulated by mechanical chopper (38) and collimated by optical element (40). The IR radiation is then projected through sample gas cell 34 and subsequently split as a function of wavelength by beamsplitter 42.

Long-wavelength IR radiation ($\lambda > 5$ $\mu$m) is reflected by optical element or beamsplitter 42 through lens 44 and narrow bandpass optical filter (NBOF) 46. NBOF 46 isolates a narrow—typical full-width half maximum (FWHM) between 1% and 5% of the center wavelength (CW)—spectral region corresponding to a suitable reference or measurement wavelength of the analyte of interest. The radiation passing through NBOF 46 is sensed by detector 48 which produces an electrical signal when illuminated by IR radiation of CW corresponding to that reflected by beamsplitter 42 and isolated by NBOF 46. The signal produced by detector 48 is amplified by detector preamplifier circuit board 50 and transmitted to the signal processing circuit board in electronics stack 52.

Shorter wavelength IR radiation ($\lambda < 5$ $\mu$m) is transmitted through beamsplitter 42 to be split again by optical element 54 which can either be another dichroic beamsplitter or 50:50 beamsplitter. The transmitted radiation is split yet again, by another 50:50 beamsplitter 56. The reflected portion of the beam is focussed by lens 60 through NBOF 62 onto detector 64 whose signal is amplified by pre-amp circuit board 66 and sent to a signal processing board in electronics stack 52.

The portion of the radiation transmitted through beamsplitter 56 is reflected off mirror 58 and focused through optical element or lens 68 onto narrow bandpass optical filter 70, detector 72 on preamplifier circuit board 66. Again, preamp circuit board 66 amplifies detector signals which are transmitted to signal processing electronics stack 52.

A second channel receives the reflected portion of the beam off beamsplitter 54 having the same components as the processing assemblies 55 and 57. These processing assemblies 74 and 76 are each comprised of beamsplitter 78 and mirror 80, lenses or optical elements 82 and 84, NBOF's 86 and 88, detectors 90 and 92, and preamplifier circuit board 94 that amplifies the output of each detector 90 and 92 to analyze the radiation transmitted by beamsplitter 54 through NBOF's 78 and 80. The output from preamplifier circuit board 94 is transmitted to signal processor located in electronics bus 52.

The analyzed fluid or gas consist of an air sample drawn continuously from a sampling point in close proximity to a subject's mouthpiece (FIGS. 12 and 13) and transferred via a short piece of tubing 30 typically having an internal diameter (ID) between 1.0 to 1.5 mm through flow rate monitoring device 32 and sample cell 34. Exhaust from sample cell 34 is directed through optional $O_2$ analyzer 96. The addition of an oxygen ($O_2$) measurement channel enhances the monitor usefulness to the medical community even further by allowing $O_2$ consumption, $CO_2$ production, and Q (i.e., cardiac output) to be monitored in one portable, cost effective device. Shading is used throughout the drawings to indicate heating in the sampling system to reduce and avoid the effect of condensation.

In essence the preferred embodiment illustrated in FIG. 3 represents a rapid, 5-channel spectrometer, with each detector 48, 64, 72, 90, and 92 observing a narrow wavelength range 100% of the time. For the purpose of Q monitoring using the $C_2H_2$ (rebreathing and/or non-rebreathing) foreign gas method, $C_2H_2$ in breath can conveniently be measured as a function of IR absorption at fundamental band 10 illustrated in FIG. 1(a). Carbon dioxide ($CO_2$) is measured either at fundamental $^{12}CO_2$ asymmetric stretch 12 or at $^{13}CO_2$ asymmetric stretch 13 illustrated in FIG. 1(b). The choice of band is largely dependent on the target $CO_2$ concentration and the optical pathlength.

For large $CO_2$ column densities the $^{13}CO_2$ peak is more useful as the $^{12}CO_2$ band becomes saturated. The relative intensity of these bands is largely dictated by the abundances of the two carbon isotopes in the exhaled breath. The natural relative abundance of these two isotopes is roughly 100:1, $^{12}C:^{13}C$. Other suitable absorption bands, such as the combination-overtone bands of $CO_2$ at 3610 cm$^{-1}$ and 3715 cm$^{-1}$ or the first overtone of the $C_2H_2$ band at 1.52 $\mu$m, can also be used to measure concentrations of these analytes in breath. These measurements can be made using commercially available NBOF's and thermo-electrically cooled lead selenide (PbSe) photodetectors.

However, $H_2O$ (i.e., moisture)—always present in exhaled breath in high concentrations, usually around 100% $R_H$—is known to interfere with $C_2H_2$ absorption band 10, leading to potential biasing of the readings. This is a serious limitation of common commercial IR $C_2H_2$ analyzers. Thus, moisture is measured in the preferred embodiment of the invention shown in FIG. 3, by monitoring $H_2O$ absorption band 14 (FIG. 1(c)) or another suitable peak, and this $H_2O$ measurement is used to compensate $C_2H_2$ readings for $H_2O$ interferences. This analytical approach is possible as the interference effects are additive.

The choice of detection system for measuring $SF_6$ band 16 (FIG. 1(d)) at 945 cm$^{-1}$ (i.e., long wavelength IR) represents a key innovation in the invention disclosed herein. The major drawback of the IR photodetectors measuring radiation in the wavelength exceeding 5.5 $\mu$m is the need for $LN_2$ cooling to suppress thermal generation of free carriers resulting in noise. Typically, cryogenically cooled detectors (e.g., mercury-cadmium-telluride photodetectors) would be employed, which would not be practical here as $LN_2$ is not usually available in remote locations. The cost of such detectors is also prohibitively high. Thermopiles and pyroelectric detectors are low-cost devices and can measure long wavelength IR, but their response times typically are too slow for this application. A new generation of photodetectors for long-wave IR spectroscopy that only require thermo-electric cooling have recently emerged and are now sold commercially (e.g., Boston Electronics, Brookline, Mass., Electro-Optical Systems, Phoenixville, Pa., and Infrared Associates, Stewart, Fla.).

These devices primarily consist of mercury-cadmium-telluride (HgCdTe) and mercury-cadmium-zinc-telluride (HgCdZnTe) photodetectors, and can be immersed in high refracted index hyperhemispherical CdZnTe lenses to improve signal to noise ratio. Another recent development includes mounting the detector element at the focus of a miniature (diameter approximately 8 mm) gold-plated parabolic mirror, which is sealed in the detector package and thermally grounded to the thermo-electric cooler. This significantly helps the optical delivery to the detector and avoids the need for focusing optics in front of the detector, which can now be placed directly in the collimated IR beam. Mercury-cadmium-telluride detectors have good performance specifications and 950 cm$^{-1}$ such as a D* exceeding 1.0×10$^8$ cm Hz$^{1/2}$ W$^{-1}$ (e.g., Model MCT-TE3-110.6-1.0 Infrared Associates) and a response time below 5 nsec. Monitoring $SF_6$ at its fundamental absorption therefore is possible at very high modulation rates without the need for $LN_2$ cooling.

In a preferred embodiment of the disclosed invention, dichroic beamsplitter 42 consists of a high reflectivity carbon dioxide laser mirror such as a Model No. IHR-2503 Z 10.6-45 sold by Lambda Research Optics (Cerritos, Calif.). Detector 48 preferably consists of a TE-cooled HgCdZnTe (Model No. BCI-2TE-12, Boston Electronics) or a HgCdTe (e.g., Model No. MCT-TE3-10.6-1.0, Infrared Associates) detector. NBOF 46 isolates a spectral region suitable for $SF_6$ measurement, such as the 955–925 cm$^{-1}$ range 16 as shown in FIG. 1(d). Pre-amp electronics 50 are based on ultra-low voltage noise op-amps (e.g., Model No. LT1028 produced by Linear Technology, Milpitas, Calif.) followed by a three-stage gain block to achieve maximum gain-bandwidth capability of 100 GHz. Detector thermostasis is precisely controlled (control stability approximately 0.01° C.). Optical element 44 can comprise a suitable lens (e.g., plano-convex lens) or lens system, or a focusing mirror. In the case of detectors having a parabolic mirror built into the detector package, such an optical element may not be necessary.

Rapid response time (in the range of 10–50 msec, 10–90%, or faster) is an important feature of the invention disclosed herein. The monitor therefore is designed with this specification in mind. IR beam emitter 36 is modulated by mechanical modulator 38 either an optical mechanical chopper or an electro-optical shutter, at rates exceeding 500 Hz, typically around 2,000 Hz. Detectors 48, 64, 72, 86, and 92 accommodate these rapid modulation rates.

In another embodiment of the disclosed invention all detectors consist of rapid pyroelectric detectors such as the PY45 series (SensArray, Burlington, Mass.) of lithium tantalite detectors. When pyroelectric detectors are employed, it is possible for all detectors 48, 64, 72, 90, and 92 to be identical, as well as the corresponding pre-amp circuit boards 50, 66, and 94.

In certain instances the radiation from two emitters is combined via a suitable beamsplitters or fiberoptic cable. For example, the light emitted by a broad-band thermal element may be combined with the output of a miniature $CO_2$ laser, such as a Model LASY-1 manufactured by Access Laser Company, Marysville, Wash., in order to boost the intensity of the photon flux at wavelength corresponding to the $SF_6$ absorption band. The combined radiation usually is modulated together but can also be modulated separately.

In the preferred embodiment of the disclosed invention, beamsplitter 54 consist of a dichroic beamsplitter. For instance, IR radiation wavelength longer than 3.4 μm (2875 cm −1) is reflected, whereas radiation of shorter wavelength is transmitted.

In another embodiment, a 50:50 beamsplitter, where no significant wavelength discrimination in the mid-IR occurs is employed. When the above dichroic beamsplitter is employed, NBOF 86 is used to isolate a spectral bandpass suitable as a reference for all measurements such as the 4.00–4.10 μm (2500–2440 cm −1) region. NBOF 88 is used to isolate a spectral range corresponding to the $CO_2$ absorption peak, such as band 12 and/or band 13 shown in FIG. 1(b). Detectors 90 and 92 consist of TE-cooled PbSe detectors (e.g., Model No. BXT2S-18T(E), CalSensors, Santa Rosa, Calif.) mounted on pre-amp circuit board 94. Pre-amp circuit board 94 is based upon a low-noise field effects transistor (FET) op-amp (e.g., Model No. AD822, manufactured by Analog Devices, Norwood, Mass.) and detector thermostasis maintained to within 0.01° C. The circuit also includes a high stability and low noise bias DC supply. NBOF's 62 and 70 are used to isolate acetylene band 10 and water band 14, respectively, as shown in FIGS. 1(a) and 1(c). Detector signals from detectors 64, 72, 90 and 92 are amplified and transmitted to electronics stack 52 for processing.

Thermal stability of the device is also important especially for field use. All detectors are thermally grounded to a common aluminum heat sink, thus insuring they experience an equivalent thermal environment. All signals transmitted through cable connection 98 are transmitted to electronics stack 52 of circuit boards (FIG. 16).

Figure 16:
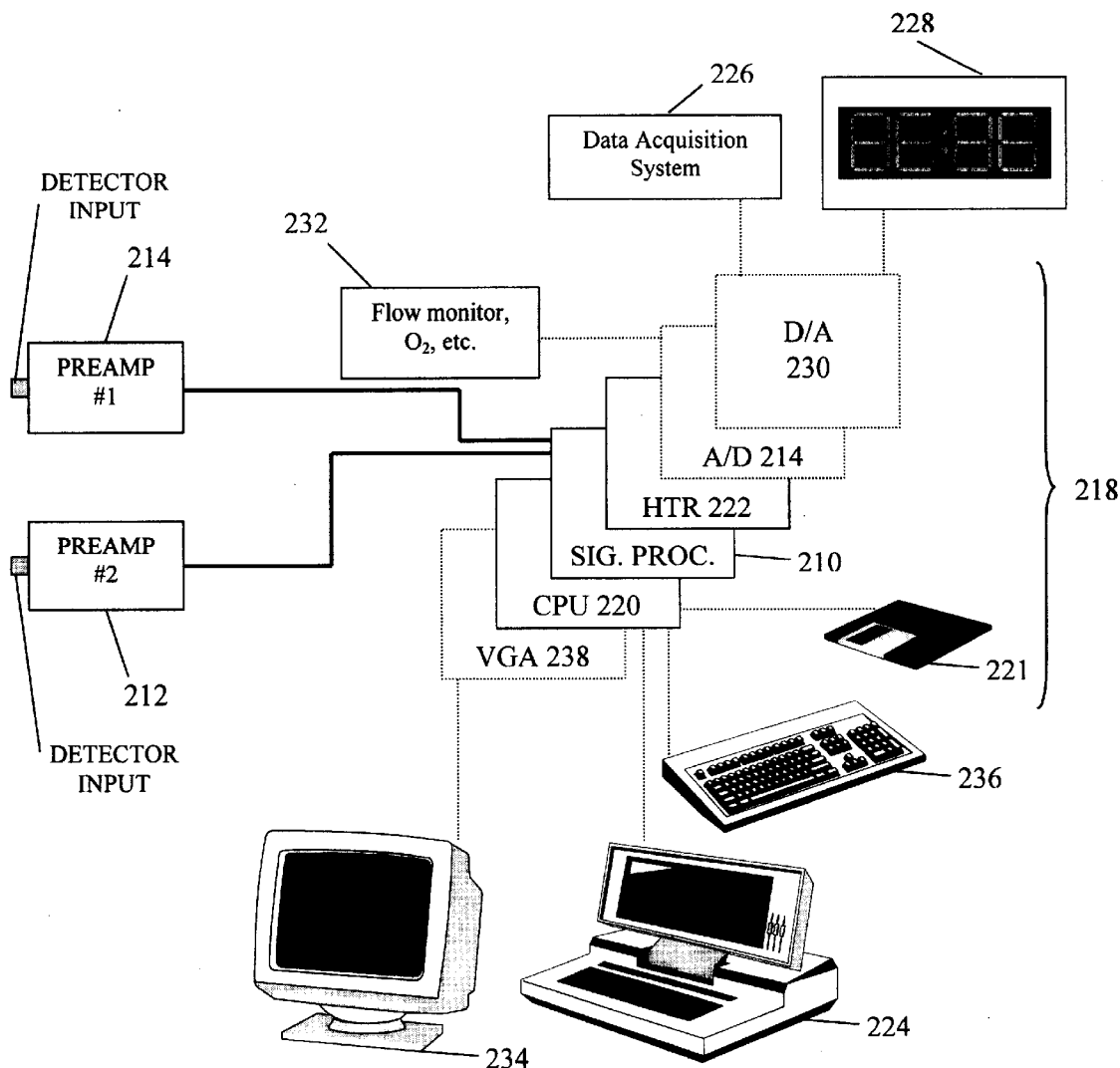
FIG. 16 is a semi-schematic block diagram illustrating the electronics stack for processing the data.

A two-detector channel system is illustrated in the semi-schematic diagram of FIG. 16. In a preferred embodiment of the disclosed invention, each signal processing board 210 is able to process signals from two detector preamp boards, 212 and 214. Multiple signal processing boards can be used on one stack. The signal processing approach is comprised of high frequency (e.g., 2,000 Hz) synchronous rectification (demodulation) followed by analog to digital conversion. Digitization can be obtained using Model No. AD7714 analog-to-digital converter (ADC) from Analog Devices having a programmable resolution (16–24 bits), gain (1× to 128×), and speed (5–60 Hz). Note that the signals from all detectors are amplified, filtered, and digitized in parallel by the multichannel (one for each detector) signal processing electronics 210. The duty cycle for each channel is 100%, thereby leading to rapid, continuous measurements. Optional heater controller board 222 manages one or more temperature and pressure control loops (e.g., to maintain the temperature and pressure of the sample cell) and can also measure a number of analog inputs. In one configuration, all signal processing boards are mounted on one common PC-104 bus 218, taking advantage of its miniaturized configuration. Using this approach, of-the-shelf computer boards can be plugged into the stack to perform a variety of useful functions. CPU board 220 manages the system and contains digital outputs (e.g., RS-232), which can be interfaced with a radio modem for telemetry applications; keyboard 236, lap-top PC 224 and storage device 221 all interface directly to the CPU board. VGA card 238 enables desktop monitor 234 to be connected to the stack. Analog-to-digital (A/D) conversion circuit board 214 is used to input analog signals (e.g., flow, pressure, and temperature measurements, and signals from $O_2$ monitor) into the analyzer and can also be used to signal the analyzer when a valve is switched. Digital-to-analog (D/A) conversion circuit board 230 is used to output signals from the analyzer to external devices (e.g., data acquisition system 226, display panel 228) and to provide signals (e.g., 5 V DC) for contact closures (e.g., switching valves). The complete system is powered by power supply (97), shown in FIG. 3.

In another configuration, PC-104 stack 218 is substituted by an electronics stack where cards 238, 220, 214, and 230 are replaced by a customized CPU board 220 designed around a suitable microcontroller, such as the HC12 (Motorola Semiconductor Products, Austin, Tex.) including 128 KBy of RAM, 128 KBy of E/EEPROM, and a 16 bit ADC. The CPU board used in this configuration also contains the necessary A/D, D/A functions described above as well as the digital output ports and interfaces for external storage devices. Signal processing board 210 and heater controller board 222 plug into customized CPU board 220 and can be used in a similar fashion to that described above.

Miniature optics (12.7 mm diameter, or less) are employed to minimize instrument size and volume of sample cell 34. Sample cell 34 can comprise a sample compartment permitting sample cells of different depths, (e.g., 1–100 mm) and hence optical pathlengths to be easily substituted. Gas chromatography IR light tubes can also be used as sample cells as these devices afford low volume-high optical pathlength combinations. A light tube consists of a hollow tube coated to allow light of the designed wavelength to be reflected multiple lines internally. Since optical absorption by gaseous analytes are linearly dependent on optical pathlength, instrument sensitivity can be tuned at the expense of response time. The thicker the cell, the higher the volume and the slower the instrument response time. For example, in certain cases it is desirable to obtain as much intra-breath (i.e., within a single breath) information is possible. In these instances a very fast response time (e.g., 10 msec. 10–90%) is desirable. In general, the volume of the sampling system is below 1.25 mL.

Analog inputs of expiratory breath and sample flow rates, sample cell pressure, and temperature, analog output capabilities, as well as an RF modem may be included interfaced to PC 104/electronics stack 52, as described above. Data is either logged directly in the analyzer (e.g., to a disk-on-chip or "Flash"), allowing convenient access following the experiment, sent digitally to an external lap-top PC 224 (e.g., via Ethernet or RS-232), or transmitted to data acquisition system 226 as analog signal (e.g., 4–20 mA) via D/A board 230 (in the case of the PC-104 configuration).

Condensation of volatiles in the sampling system is avoided by controlling temperature to approximately 45° C. and pressure approximately 760 Torr). Sample flow rates vary depending on the rebreathing (or non-rebreathing) apparatus, but are typically between 20 and 2,000 mL min$^{-1}$. At higher flow rates, the sample may be recycled back into the anesthetic bag (i.e., gas reservoir). Flowmeter 32 measures sample flow rates. In some cases, it may be desirable to use a small particulate trap upstream of flowmeter 32.

Another important feature of the disclosed invention lies with its inherent flexibility. Only minor hardware modifications to the optical cell and NBOF's are required to measure the concentration of carbon monoxide (CO), nitrous oxide ($N_2O$), and ammonia ($NH_3$) and acetone in breath by monitoring the intensity of the absorption bands 18, 20, 22, and 24, respectively, shown in FIGS. 2(a) through 2(d). Any other analyte with a suitable absorption band in the UV-visible-IR (i.e., 185–20,000 nm) can be monitored by analogous means.

Thus, the invention disclosed herein has numerous breath analysis applications outside the Q monitoring area, as discussed above. In some cases, a long optical path length greater than 10 cm may be used to achieve the desired sensitivity. In such cases, multipass cells based on the design described by White (White, J. U. J. Opt. Soc. Am. 1942, 32, 285–288 incorporated herein by reference) may be used in lieu of a single pass cell. Multiple pass optical cells have the advantage of combining long optical pathlengths with relatively low sample volumes.

Figure 4:
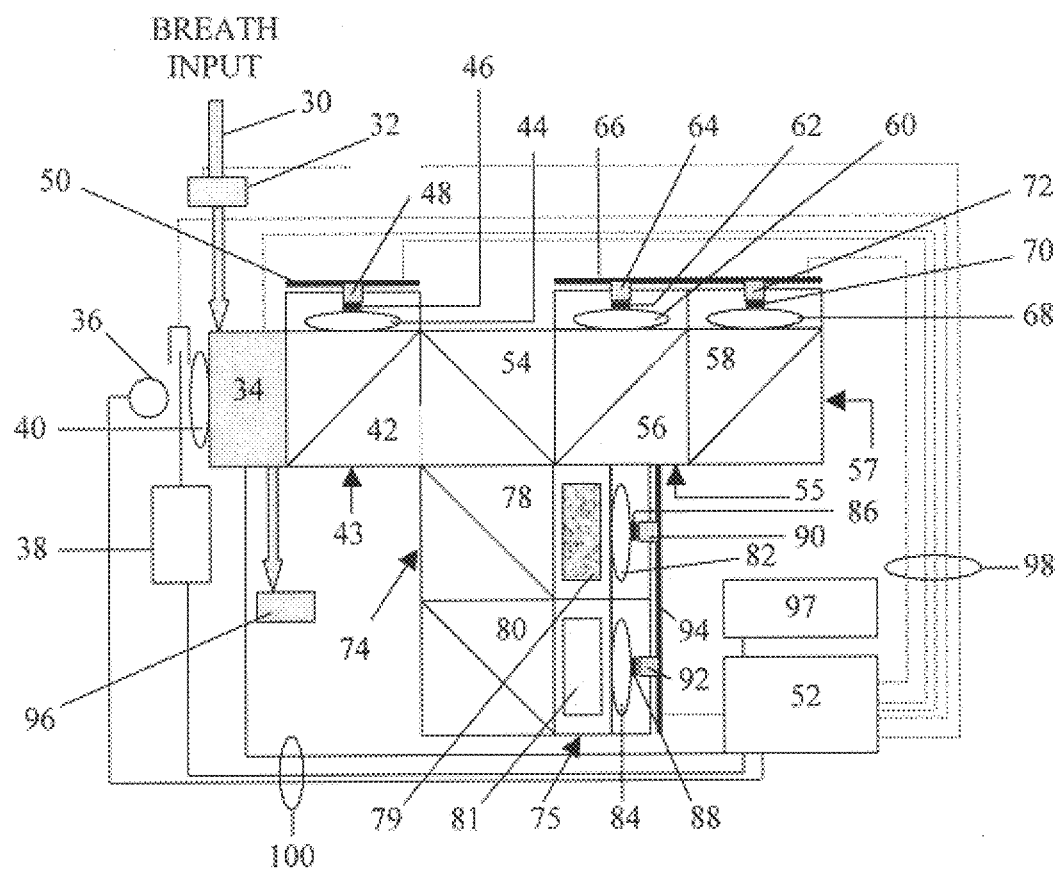
FIG. 4 is a schematic block diagram of a second embodiment of the invention similar to the first embodiment of FIG. 3 except for the addition of an optical cell having a gas cell filled with an analyte of interest for use in gas filter correlation (GFC) spectroscopy.

An alternate embodiment of the invention is illustrated in FIG. 4 where $C_2H_2$ is monitored by a technique known as gas filter correlation (GFC) spectroscopy which has been used extensively for monitoring CO in ambient air and stack gases. This approach can be used whenever a gas absorption band possesses sufficient fine structure, such as the bands 10, 12, 13, and 14 in FIGS. 1(a) through 1(c), and the bands 18, 20, and 22 illustrated in FIGS. 2(a) to 2(c). In the embodiment of FIG. 4, like elements are indicated by like reference numbers as the embodiment illustrated in FIG. 3. In this embodiment, optical chamber 75 is inserted between beamsplitter 78 and mirror 80 and lenses 82 and 84. Optical chamber 75 contains two gas cells. One gas cell 81 is filled with a non-absorbing gas (e.g., nitrogen ($N_2$) or helium (He)), while the other 79 is filled with high concentrations (often 100%) of the analyte of interest, in this case $C_2H_2$. Gas filled cell 79 is placed in front of reference detector 90. In some cases, gas cell 81 may be sealed under vacuum (P<1 Torr), or may be omitted completely. NBOF's 86 and 88 in front of reference detector 90 and sample detector 92 are identical with the embodiment shown in FIG. 3 and are chosen to overlap with the acetylene absorption feature 10. The details of signal processing when using the gas filter correlation spectroscopy technique are illustrated in flow diagram of FIG. 15 which will described in greater detail hereinafter.

Figure 5:
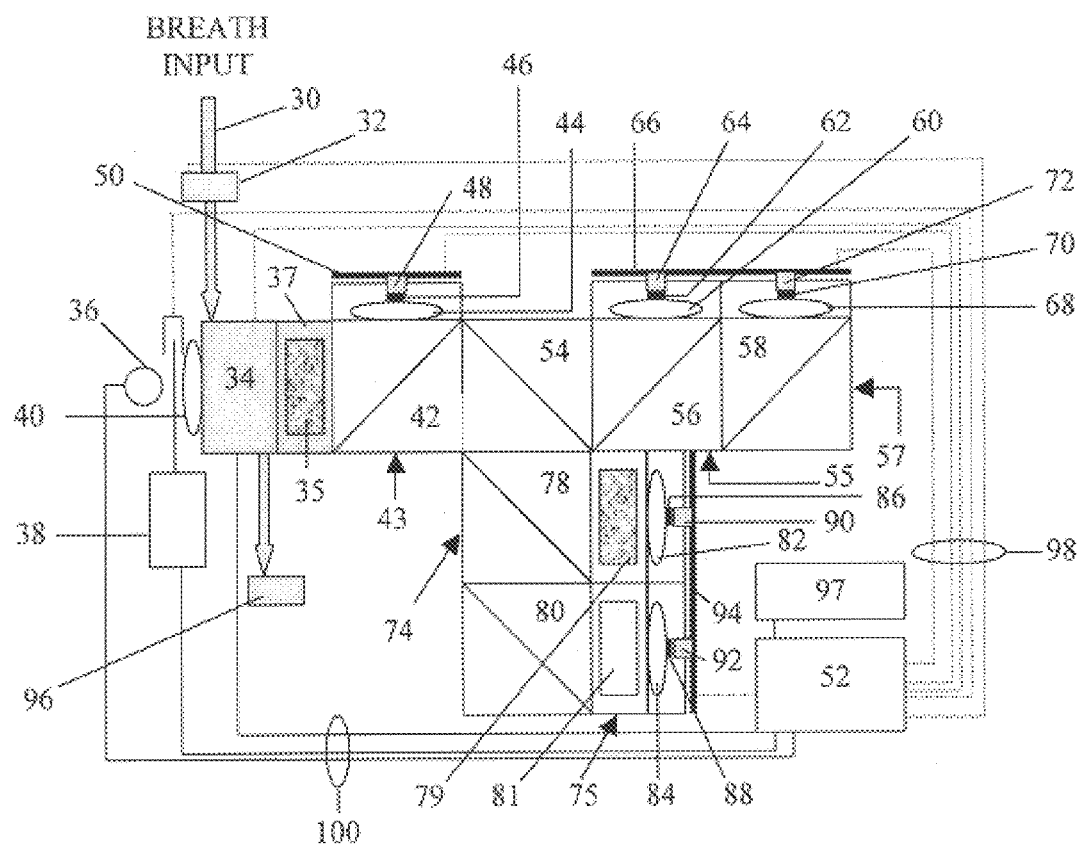
FIG. 5 is a schematic block diagram of another embodiment of the invention similar to the embodiment illustrated in FIG. 4 with the collimated IR radiation beam first directed through an optical chamber containing an optical cell filled with water vapor.

Another preferred embodiment of the invention is illustrated in FIG. 5 substantially similar to the embodiment of FIG. 4 wherein like reference numbers indicate like parts throughout. In this embodiment, gas cell 35 filled with $H_2O$ vapor in optical chamber 37 is inserted just downstream of sample chamber 34. The column density of $H_2O$ vapor in gas cell 35 is very large compared to that in the sample cell 34. For example, gas cell 35 could consist of a heated gas cell 50 mm deep containing 95% RH at 45° C., where as the depth of sample cell 34 is about 1 mm. The $H_2O$ in gas cell 35 is used as a negative filter, in an analogous fashion to gas filter correlation spectroscopy, to filter out all $H_2O$ absorption lines from the broadband IR radiation. The purpose of this $H_2O$ filter is to make the IR spectrometers insensitive to water vapor in the sample being analyzed. Thus, in this embodiment the acetylene channel no longer suffers from water spectral interferences and the water measurement channel can be omitted. This technique can be used in conjunction with gas filter correlation spectroscopy, as shown in FIG. 5, or with the measurement approach illustrated in FIG. 3. The disclosed method and apparatus for removing spectral interferences from the analyzer can be extended to any gas with sufficient spectral fine structure, in an analogous fashion to gas filter correlation spectroscopy. For example, $CO_2$ interferences on CO measurements can be eliminated by introducing a gas cell filled with $CO_2$ into the optical train, just downstream of the sample cell.

The modular design of the analyzer is illustrated in FIGS. 6 and 7 again where like parts are identified by like reference numbers throughout. By changing the combination of optical chambers, the instrument shown in FIGS. 3, 4, or 5 can conveniently be converted to a three-channel spectrometer 100 or a seven-channel spectrometer 102.

Interference-canceling chamber 37 and gas filter correlation chamber 75 may be added or subtracted as the application requires. For each additional detector pair, an additional signal processing circuit board is added to electronics stack 52. There is no practical limit to how many channels can be added to the system except the size of the apparatus with typically four signal processing circuit boards (eight detectors) or less used. The three-channel embodiment of FIG. 6, uses beamsplitters 56 and 57, mirror 58 and appropriate focusing optics such as lenses 44, 60, 68 and NBOF's 46, 62, 70.

Figure 6:
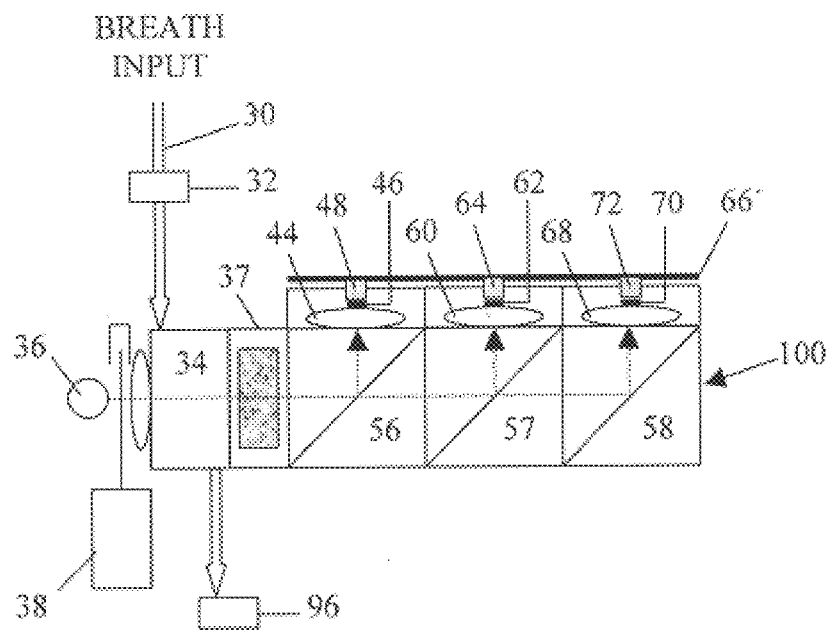
FIG. 6 illustrates the modular schematic block diagrams of the invention illustrating the modular nature of the optical mechanical design in which three detectors are used respectively.
Figure 7:
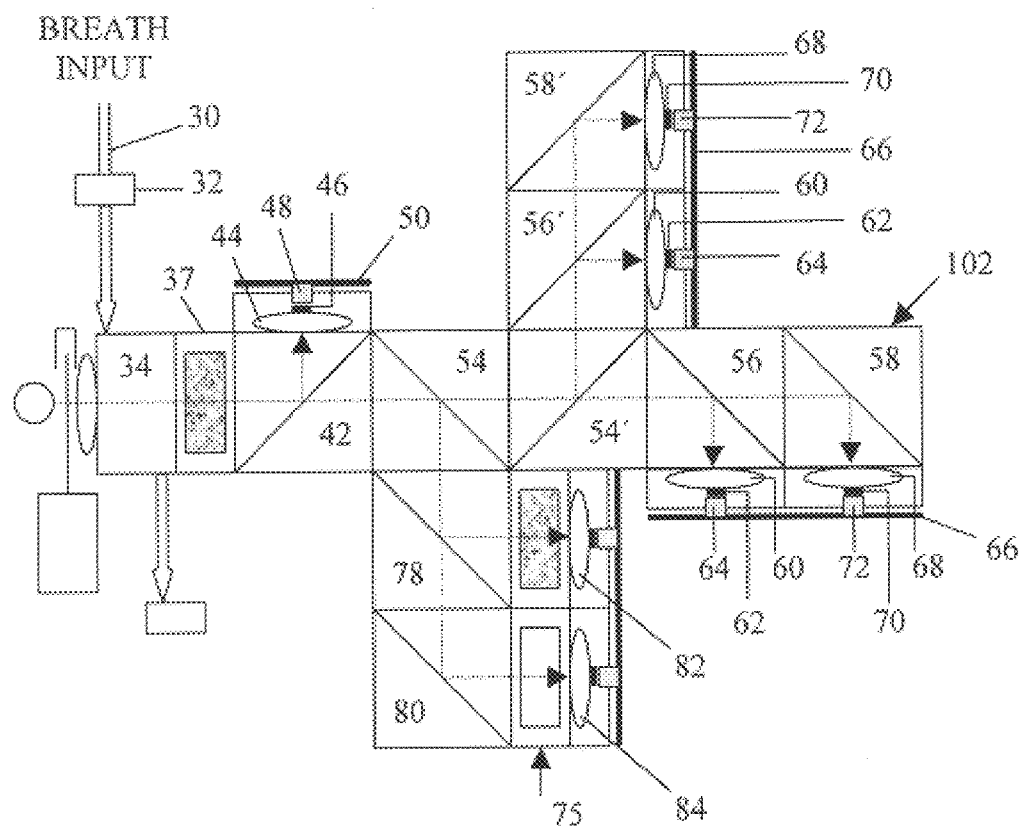
FIG. 7 illustrates the modular schematic block diagrams of the invention illustrating the modular nature of the optical mechanical design in which seven detectors are used respectively.

In the embodiment of FIG. 7, an additional beamsplitter 54' is added to split the beam to added channels 56' and 58' to increase the number of channels shown in FIGS. 5 to 7. As a practical matter, the only limit is physical size. It is the intent of this apparatus to keep it small and very portable.

FIGS. 8(a) through 8(c) are drawings of a beamsplitter or mirror optical chamber, assembly of the chamber, and connection of multiple abutting chambers, respectively. The beamsplitting or mirror chamber consists of a square block of aluminum, with interconnecting passageways 108 and 110 which intersect passageway 112, (FIG. 8(b)). Mirror or beamsplitter 114 attached to frame 116 is inserted in passageway 112 as indicated by arrow 118 at an angle of approximately 45° to each passageway 108 and 110. Frame 116 with mirror or beamsplitter 114 is inserted in passageway 112 optically aligned by rotating frame 116 and then locked by set screw 120.

Multiple beamsplitter optical chambers may be connected as illustrated in FIG. 8(c). The three interconnected passageways 108 and 110 are milled out to allow light to be projected through the openings to the corresponding elements, as illustrated in the preceding figures. The optical beamsplitter chambers 106 can be connected or mounted to one another and precisely positioned by positioning pins 124 as illustrated in FIG. 8(c). Each beamsplitter or mirror optical chamber or aluminum block would have four sockets 124 on each side for receiving positioning dowel pins (not shown) to keep adjacent beamsplitter optical chambers in precise alignment with one another. Bracket 126 locks adjacent beamsplitter optical chambers together in proper alignment using screws 121 in threaded holes 122. Positioning dowel pins in adjacent sockets 124 insure precise optical alignment with clamping plate 126 holding the chambers together in an assembled structure.

Mirror or beamsplitter 114 is mounted in holding frame 116 which is inserted through opening 112 into the beamsplitter chamber to intersect passageways 108 and 110. The optical alignment of the mirror 114 can be adjusted conveniently by rotating holding frame 116 and then fixing its position by means of set screw 120. Optical chambers housing sample cells, gas cells, lenses, and detectors are all made of aluminum and have matching designs. This approach insures minimal effort to achieve optical alignment, as well as a compact, sturdy assembly of all optical components that is insensitive to dust and vibration. As all optomechanical parts are made of aluminum and are thermally grounded to one another, thermal management of the system is easily achieved. When operating the analyzer in environments where large temperature fluctuations exist, a heater may be used to control the temperature of the assembled chambers to maintain instrument stability.

Figure 9:
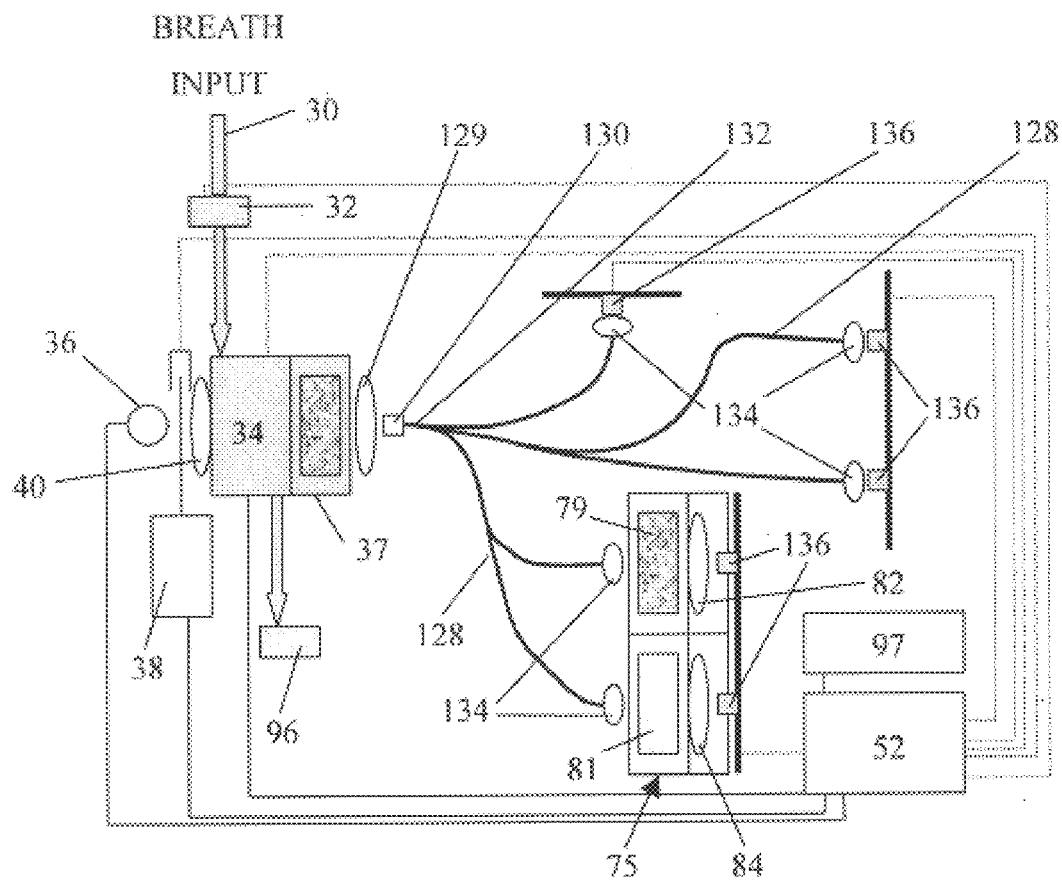
FIG. 9 is a schematic block diagram of the invention similar to FIG. 5 with beamsplitters replaced by optical fibers and a single optical element.

Another optional but preferred embodiment of the invention is illustrated in FIG. 9 in which like reference numbers indicate like parts throughout. In this embodiment, the multiple beamsplitters illustrated in embodiments of FIG. 3 through 7 and replaced by a bundle 132 of appropriate optical fibers 128. IR radiation from source 36 emerging from optical chamber 34 and optical chamber 37 is collected by optical element 129 and 130 which projects the radiation into fiber bundle assembly 132 for distribution by optical fibers 128 to each channel. Optical element 129 and 130 may be a mirror or lens systems. Light is channeled via fibers 128 to optical elements 134 in each channel that couples the output from optical fiber 128 to detectors 136 and through GFC assembly 75 to detectors 136. Fiber assembly 132 either consist of single fibers or multiple fiber bundles 128 and are generally sheathed in a plastic jacket. Flexible metal sleeves are sometimes used with the more brittle fibers to offer extra support. The individual optical fibers 128 in fiber optical assembly 132 typically terminate with SMA-905 connectors and interface with optical assemblies via corresponding bushings and bulkheads. Fiber optic materials must satisfy the optical (e.g., transmission), mechanical (e.g., flexibility, such as a bend radius 200× the fiber radius, and strength), and economic requirements of the application. Fiber diameters can vary between 50 and 500 $\mu$m. Suitable materials consist, but are not limited to, a family of glasses, such as—suitable spectral transmission range given in brackets—Sapphire (2–4 $\mu$m), ZBLAN (0.25–4 $\mu$m), AsGeSeTe (4–11 $\mu$m), PC AgBrCl (3–16 $\mu$m), hollow silica waveguide (0.9–25 $\|$m), and others.

Figure 10:
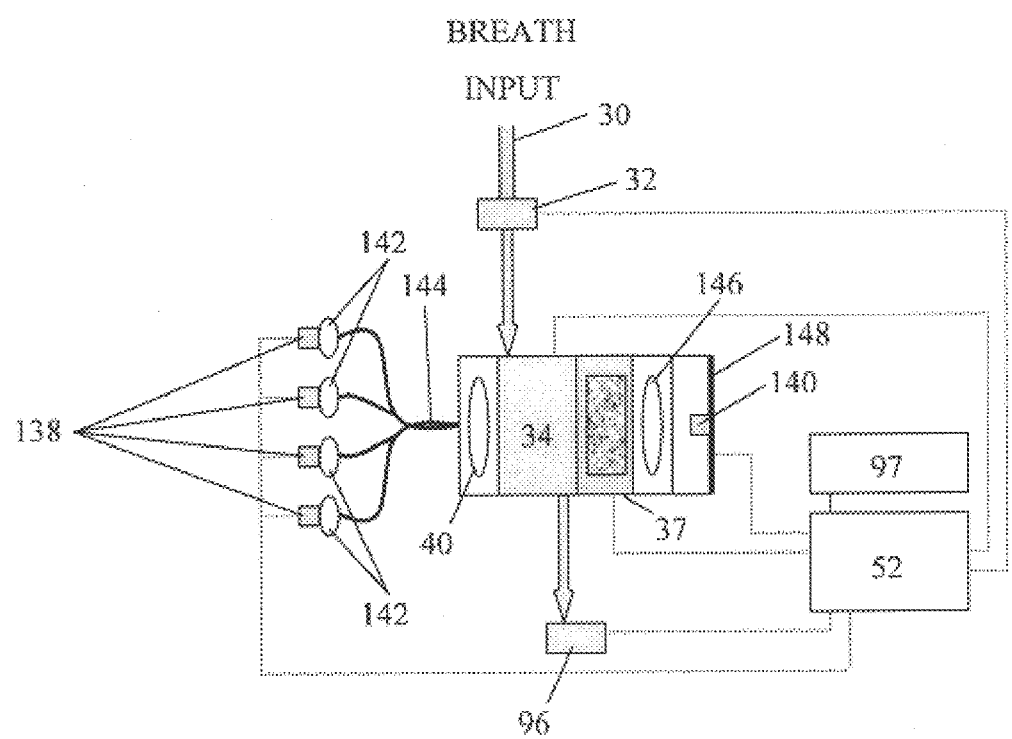
FIG. 10 is a schematic block diagram of the invention in which optical fibers are used to channel radiation from multiple IR sources to a single detector.

Another alternate arrangement of the invention disclosed herein is illustrated in FIG. 10. In this configuration, the emission from multiple radiative sources 138 is distributed to a single detector 140. The remaining features are substantially similar or nearly identical to those described previously. Radiation from multiple sources 138 is collected by optical elements 142 and injected into optical fiber bundle 144. Optical elements 142 will depend on the nature of radiative sources 138. The combined radiation from all emitters 138 is projected through the gas analysis system and measured by detector 140. The radiation from sources 138 passes through lens 40, sample cell 34, and chamber 37 and is received by detector 140 from lens 146. The signal generated by detector 140 is amplified by preamp circuit board 148 and processed according to the method similar to those described above. The output from the preamp circuit board 148 is delivered to stack electronics comprised of PC stack 52.

IR sources 138 can consist of a pulsable broadband emitter (e.g., Model No. SVF360-8M, CalSensors, or Model No. NL8LNC, Ion Optics, Waltham, Mass.), an IR light emitting diode (LED), (suppliers include: Telcom Devices Corporation, Camarillo, Calif. and Laser Monitoring System Ltd., Devon, England), a superluminescent diode (supplier: Sarnoff Corporation, Princeton, N.J.), a narrow-band semiconductor incandescent source (Ion Optics, Waltham, Mass.), a tunable diode laser, a tunable quantum cascade laser, a pulsed miniature carbon dioxide ($CO_2$) laser, or any other emitter of radiation that can be electronically pulsed.

In the embodiment of the disclosed invention illustrated in FIG. 10, a circuit is employed that generates separate time-multiplexed drive signals for the array of emitters described above. The drive/excitation cycling includes one—or more—"null" intervals (all emitters "OFF") for the purpose of detector zero-level recovery. For example, with the narrow-band semiconductor incandescent emitter, the following drive parameters are used: approximately 10–50 msec. "ON-time" duration per emitter, with a 20–300 msec. array sequence cycle time. The drive signals are approximately 10–100 mA at 1–5 V. These emitter drive electronics are located at electronics bus or stack 52. The detector pre-amp circuit board 148 is essentially the same as the detector boards previously described, with a modification to accommodate detector response to the resulting radiation waveform.

A new signal processing circuit is employed that recovers/demultiplexes the detector board output composite transmittance sequence consisting of two to six intensity signals specific to each of the individual emitters 138 in the array. This allows all emitters to be processed separately using one single detector without the need of any optomechanical devices, such as a rotating optical filter wheel. The signals are then digitized by high precision electronics, such as those described above.

Figure 11:
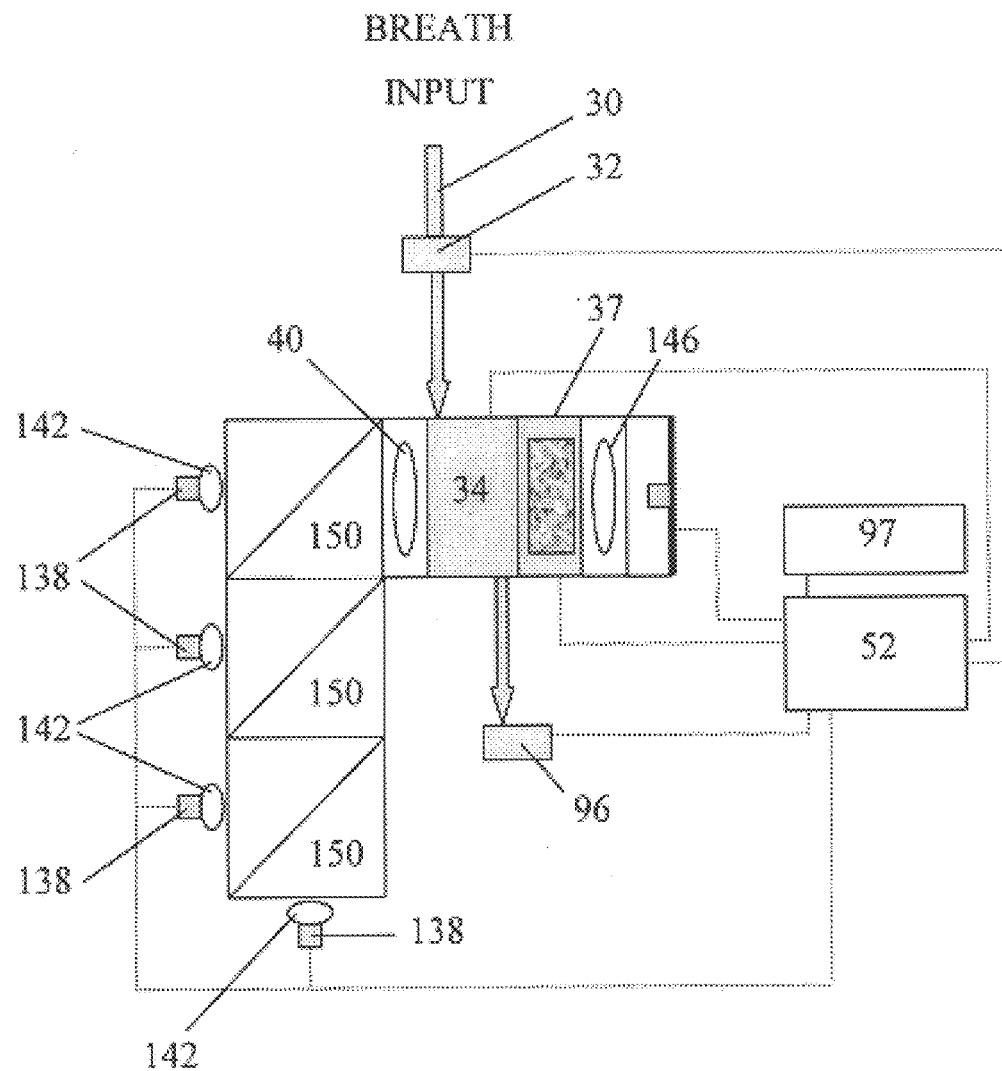
FIG. 11 is a schematic block diagram of the invention similar to the embodiment illustrated in FIG. 10 with beamsplitters used to combine independent IR beams instead of optical fibers.

Another alternate arrangement of the invention disclosed herein is illustrated in FIG. 11 and in this embodiment, beamsplitters 150 are used instead of optical fiber bundle 144 to combine the IR radiation from pulsed emitters 138. Beamsplitters 150 are either 50:50 or dichroic, depending on wavelength of the incident radiation.

Figure 12:
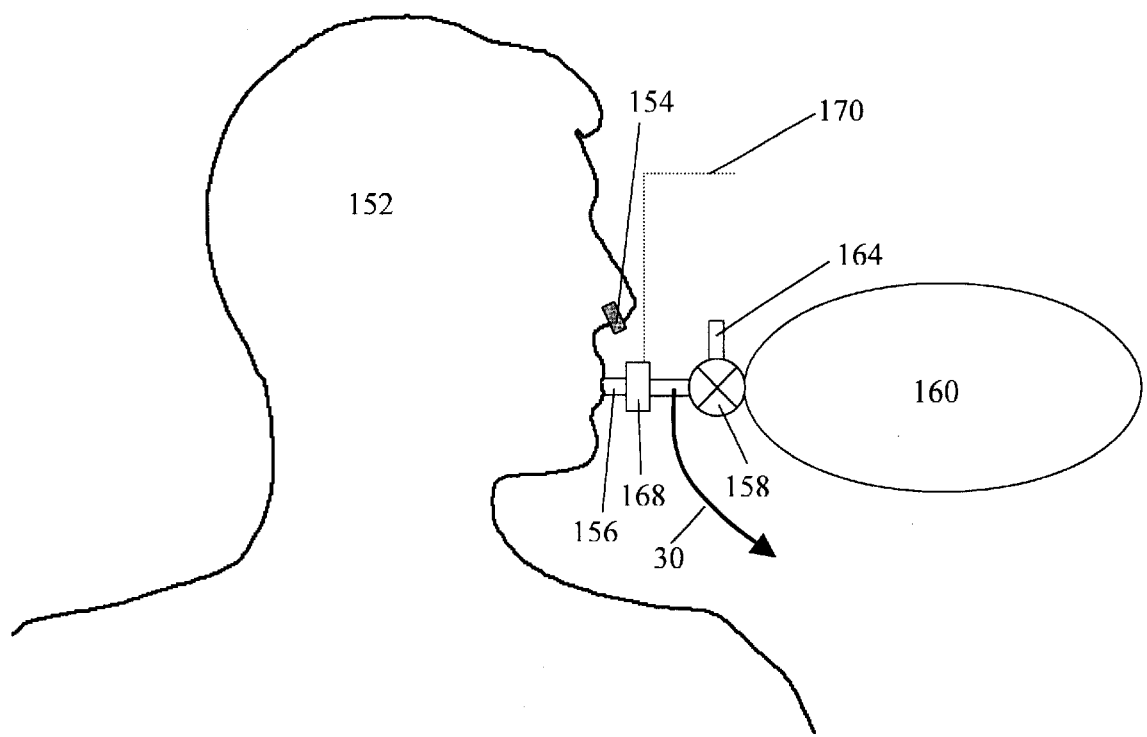
FIGS. 12 and 12(a) are schematic diagrams illustrating a rebreathing apparatus used in conjunction with the disclosed invention.
Figure 12A:
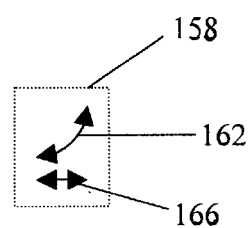

A typical setup for breath analysis is illustrated in FIGS. 12 and 12(a). This setup uses rebreathing Q monitoring with the disclosed device to collect a sample from subject 152. A subject or patient 152 having their nose occluded with a clip 154, breathes from/into mouthpiece 156, connected via three-way valve 158 to anesthetic (rebreathing) bag 160 (volume typically 1–10 L). Valve 158 typically consists of a pneumatic valve for rapid switching, although a manual valve can also be used. Pneumatic and/or solenoid valves 158 can be energized directly from the analyzer, via an analog output or contact closure. This also enables the monitoring cycle to be automatically synchronized with the switching of the valve. The valve positions during the breath analysis used in monitoring process, are illustrated in FIG. 12(a).

The measurement begins with valve 158 in position 162 drawing (i.e., breathing and exhaling) room air through tube 164. Valve 158 is then switched to position 166 and the air mixture from rebreathing bag 160, typically consisting of approximately 2% $C_2H_2$, $SF_6$, respectively, and 20–30% $O_2$ (balance nitrogen), is inhaled by subject 152. Subject 152, either at rest or undergoing exercise, breathes from, and back into, rebreathing bag 160 for the duration of the test, typically less than 60 seconds. Expiratory flow rate is measured by turbine flowmeter 168, and the signal is transmitted to the analyzer via connection 170. During the entire measurement cycle, a small sample is continuously extracted from a suitable point adjacent to mouthpiece 156 and aspirated/pumped to the monitor via tube 30. At high flow rates, the exhaust from the analyzer can be recycled into the rebreathing system just downstream of the sampling point, prior to valve 158.

Figure 13:
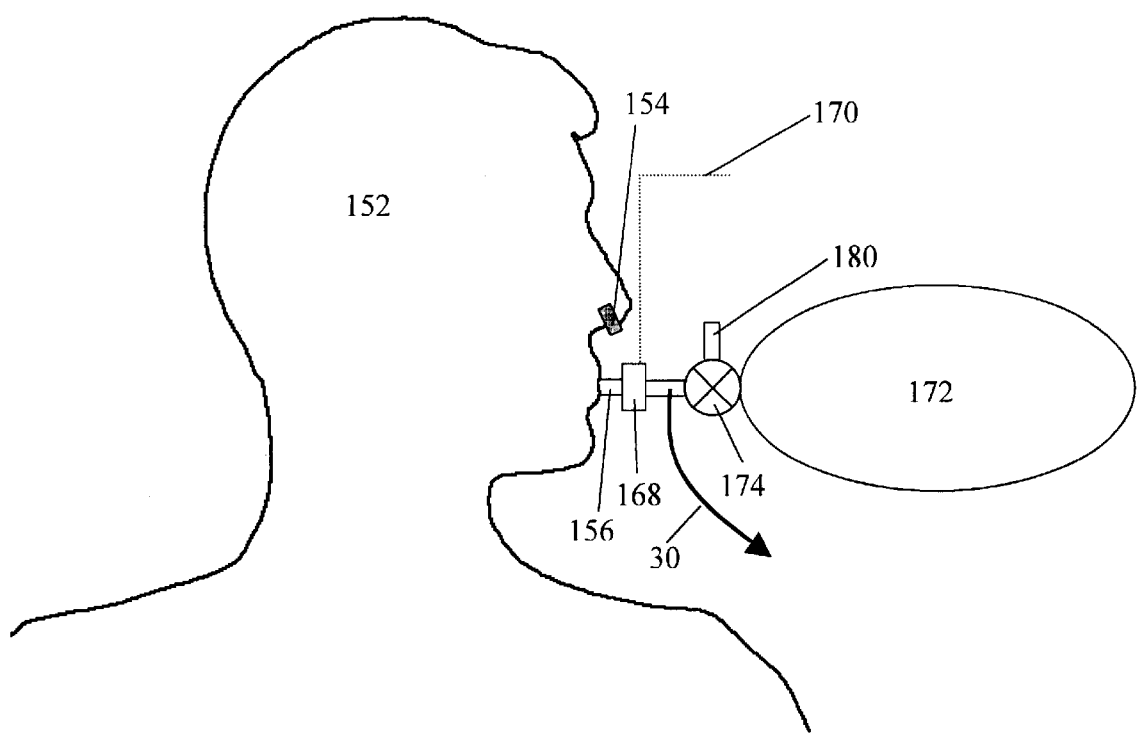
FIGS. 13 and 13(a) are schematic diagrams similar to FIG. 12 for a non-rebreathing Q monitoring apparatus.
Figure 13A:
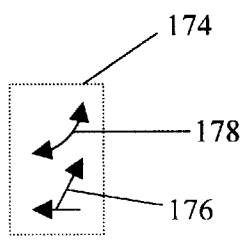

An alternate arrangement for non-rebreathing breath analysis and monitoring is illustrated in FIGS. 13 and 13(a) in which non-rebreathing Q monitoring to collect a breath sample is achieved with an apparatus similar to that shown in FIG. 12. Non-rebreathing bag 172 usually has a volume of approximately 200 L and a three-way valve 174 allows subject 152 to inhale and exhale ambient room air with valve in position 178 illustrated in FIG. 13(a). When testing begins valve 174 is switched to position 176 and subject 152 inhales an air mixture from bag 172 and exhales to ambient atmosphere via nozzle 180. Non-rebreathing bag 172 is typically filled with 2% $C_2H_2$, $SF_6$, respectively, and 20–30% $O_2$ (balance nitrogen). A sample is continuously extracted from a suitable point adjacent to mouthpiece 156 and aspirated/pumped to the monitor via tube 30.

Figure 14:
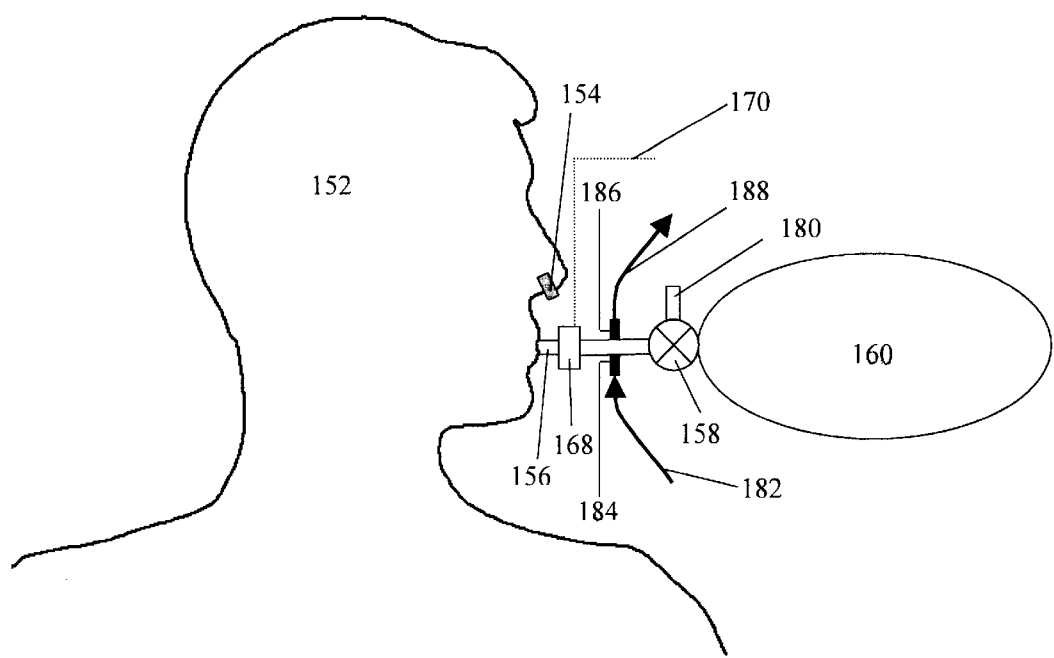
FIG. 14 is a schematic diagram illustrating an alternate optical sampling strategy that can be employed for both rebreathing and/or non-rebreathing by an arrangement of optical fibers directly transmitting IR radiation to and from a mouthpiece.

An alternate optical sampling strategy that can be employed for both rebreathing and/or non-rebreathing Q monitoring is illustrated in FIG. 14. Radiation from radiative emitters is transmitted via optical fibers 182 to a suitable bulkhead 184 mounted in mouthpiece 156. Bulkhead 184 may contain collimating optics, such as a plano-convex lens. Another bulkhead 186 containing focussing optics, such as another plano-convex lens, is connected to the mouthpiece directly opposite bulkhead 184. Optical fiber bundle 188 channels the IR radiation back to the instrument where it is analyzed.

This in-situ monitoring approach avoids the use of an extractive sampling system to collect a sample, and has the advantage of high precision—due to the long (approximately 30 mm) optical pathlength across the mouthpiece—in conjunction with very fast response times, since a sample no longer needs to be pumped to an external optical cell.

Figure 15:
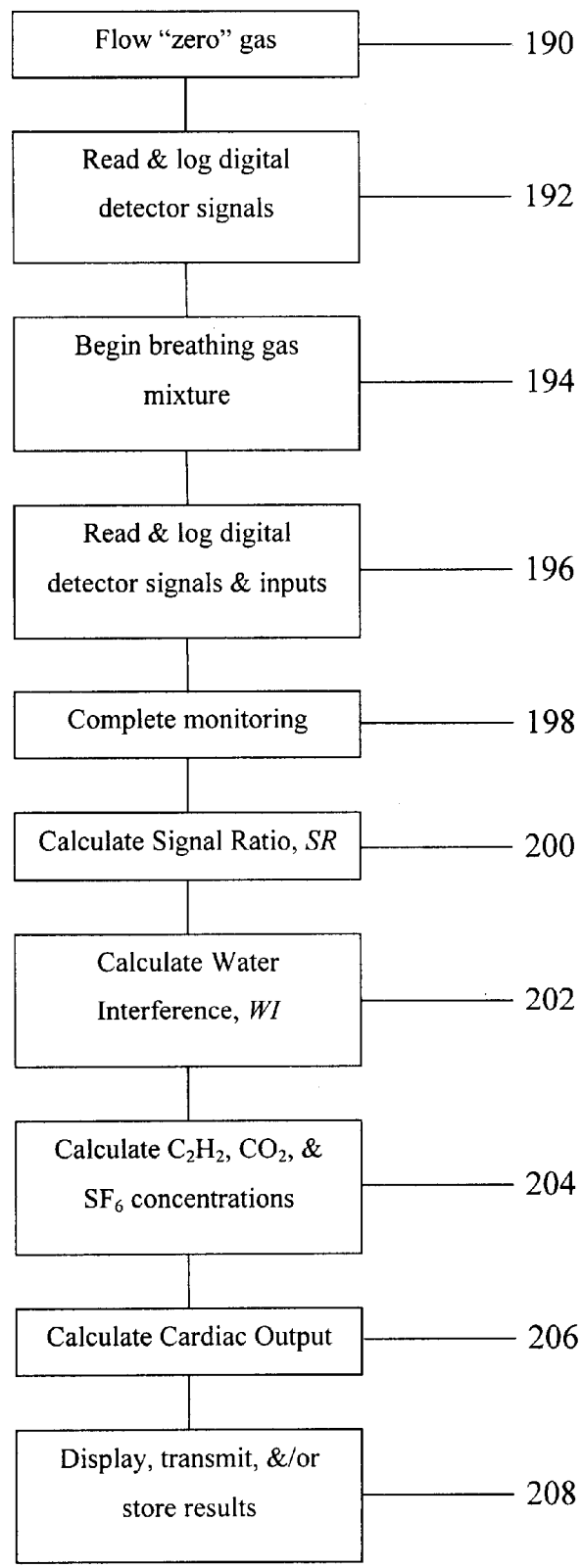
FIG. 15 is a flow diagram of the digital data processing for making Q measurements.

The signal processing methodology employed in the disclosed invention is shown in the flow diagram of FIG. 15. First, "zero" gas is introduced 190 into the analyzer for a baseline calibration. Zero gas can be nitrogen ($N_2$) or air from a cylinder, or ambient air with $CO_2$ scrubbed out. For field usage, the instrument is supplied with a $CO_2$ scrubber containing a suitable chemical reagent. During zero calibration, the average (approximately 1–5 sec.) digitized detector signals are logged to memory 192. A zero calibration typically takes less than 10 sec. to perform. As a subject begins to breathe the gas mixture in reservoir 194, a key is pressed (e.g., on laptop 224 or keyboard 236) to initiate logging of digital detector counts, as well as analog inputs (e.g., breath flow rate, sample T & P, and $O_2$ measurements) to a storage device 196. Once monitoring is complete 198, typically within 60 sec., a key is pressed at the analyzer to initiate data reduction. Signal ratio, SR, 200 is calculated according to the following Equation 1 or Equation 2, depending on the measurement approach. Equation 1 is used for differential optical absorption (DOAS) measurements (i.e., no GFC cells in front of the detectors), whereas Equation 2 is employed for GFC.

$$SR_x = [(S(t)_x/R(t)_x)/(S(z)_x/R(z)_x)] \qquad \text{Equation 1:}$$

$$SR_x = [(S(t)_x - R(t)_x)/(S(t)_x + R(t)_x)]/[(S(z)_x - R(z)_x)/(S(z)_x + R(z)_x)] \qquad \text{Equation 2:}$$

where, $SR_x$ is the signal ratio for analyte x, $S(z)_x$ are the average sample counts for analyte x during instrument zero-ing, $R(z)_x$ are the average reference counts for analyte x during instrument zero-ing, $S(t)_x$ are the sample counts for analyte x at time t during monitoring, $R(t)_x$ are the average reference counts for analyte x at time t during monitoring, In some cases, it may be preferable to use a slightly different approach as shown in the following Equation 3 (DOAS) and Equation 4 (GFC), respectively.

$$SR_x = (S(z)_x/R(z)_x) - (S(t)_x/R(t)_x) \qquad \text{Equation 3:}$$

$$SR_x = [(S(z)_x - R(z)_x)/(S(z)_x + R(z)_x)] - [(S(t)_x - R(t)_x)/(S(t)_x + R(t)_x)] \qquad \text{Equation 4:}$$

The interference of analyte y on analyte x is determined experimentally during instrument calibration. Typically five samples of y, evenly distributed concentrations spanning 150% of the instrument measurement range, are successively introduced into the analyzer and the response to x is recorded. A plot of SRx ($SR_{int}$) versus $SR_y$ yields quadratic Equation 5.

$$SR_{int} = aSR_y + bSR_y^2 \qquad \text{Equation 5:}$$

where, a and b are two constants determined experimentally during calibration.

When y is $H_2O$, water interference WI 202 is obtained as $SR_{int}$.

The concentration of analyte x, [x], is calculated 204 using a quadratic calibration curve, of Equation 6, generated experimentally in an analogous fashion to the calibration of interferences, except that analyte x is introduced into the analyzer and its response to x is recorded. In some cases, especially with extended optical pathlengths, a third or fourth order relationship may be required.

$$[x] = c(SR_x - WI) + d(SR_x - WI)^2 \quad \text{Equation 6:}$$

For $CO_2$ and $SF_6$ measurements using the bands shown in FIG. 1, WI=0 and can be omitted from Equation 6.

Based on end-tidal $C_2H_2$, $SF_6$, and $CO_2$ measurements, as well as the expiratory flow rate, Q can be calculated 206 using published expressions, such as Equation 7 (Warburton, D. E. R.; Haykowsky, M. J. F.; Quinney, H. A.; Humen, D. P.; Teo, K. K., Sports Med. 1999, 27, 241–260) for the rebreathing configuration shown in FIG. 11. The results are then displayed, transmitted and/or stored 208.

$$Q = \frac{\ln(F_A/F_{AO})}{\ln[(v_A + \alpha_t V_t)/(V_{AO} + \alpha_t V_t)]} \cdot \frac{V_E}{\alpha_b} \cdot \frac{60 \times 1000}{760} \quad \text{Equation 7:}$$

where, $F_A$ is the alveolar $C_2H_2$ concentration, $F_{AO}$ is defined by Equation 8 at full inspiration, $V_E$ is the expiratory flow rate, $V_A$ is the alveolar volume, $V_{AO}$ is the alveolar volume at full inspiration, calculated according to Equation 9, $V_t$ is the estimated pulmonary parenchymal tissue volume (3.5 ml cm−1 height), $\alpha$ is the solubility coefficient of $C_2H_2$ in tissue (t) or blood (b) [0.768 and 0.739 ml ml$^{-1}$ at 760 Torr, respectively).

$$F_{AO} = F_I/F_I SF_6/F_A SF_6 \quad \text{Equation 8:}$$

$$V_{AO} = (V_1 - V_D - (F_I SF_6 - F_A SF_6) \quad \text{Equation 9:}$$

where, $F_I$ is the inspired $C_2H_2$ concentration, $F_I SF_6$ is the inspired $SF_6$ concentration, $F_A SF_6$ is the alveolar $SF_6$ concentration, $V_I$ is the inspired volume, $V_D$ is the estimated dead space.

Measurements of $CO_2$ concentrations are used to convert measured minute ventilation to alveolar ventilation. Other appropriate expressions using the quantities measured by the disclosed invention can also be used to determine Q. When a non-rebreathing setup as illustrated in FIG. 12 is employed, the following expression can be used to determine the Q.

$$Q = \left[ \frac{V_E \times P_{ECO2} \times (P_{IC2H2} - P_{AC2H2})}{\lambda \times P_{ACO2} \times P_{AC2H2}} \right] \quad \text{Equation 10:}$$

where, $V_E$ is ventilation, $P_{ECO2}$ is mixed expired $CO_2$ partial pressure, $P_{IC2H2}$ is inspired $C_2H_2$ partial pressure, $P_{AC2H2}$ is $SF_6$-corrected end-tidal (alveolar) $C_2H_2$ partial pressure extrapolated back to breath 1 of the procedure, $\lambda$ is $C_2H_2$ blood-gas partition coefficient, $P_{ACO2}$ is end-tidal (alveolar) $CO_2$ partial pressure.

Ventilation can be modeled using a commercial software package (Consentius Technologies, Salt Lake, Utah). Continuous $C_2H_2$, $SF_6$, and $CO_2$ measurements are made for approximately 20–25 breaths, thus insuring a quasi-steady state.)

Monitored Q is output from the analyzer in a number of ways, including: digital transmission via the serial port (and subsequently the radio modem for telemetry applications), storage in the analyzer for subsequent retrieval, or the data is sent to a display or plotter.

This invention is not to be limited by the embodiment shown in the drawings and described in the description which is given by way of example and not of limitation, but only in accordance with the scope of the appended claims.

What is claimed is:

1. A method of monitoring a subject's breath for diagnostic analysis comprising;
    delivering a sample gas mixture to a subject;
    collecting a low volume breath sample from said subject;
    delivering said low volume breath sample from said subject to a miniature sample cell;
    projecting one or more collimated beams of radiation through said miniature sample cell;
    isolating a narrow spectral region corresponding to at least two selected frequency components centered at different wavelengths;
    analyzing said selected frequency components of said collimated beam with one or more spectrometers;
    storing each output from said one or more spectrometers;
    converting said outputs from each spectrometer to concentration readings;
    whereby said outputs can be processed to produce diagnostic information.

2. The method according to claim 1 in which said gas mixture is a mixture of $C_2H_2$ and $SF_6$ balance of oxygen and nitrogen.

3. The method according to claim 2 in which said step of analyzing selected frequency component comprises isolating the spectral windows corresponding to an absorption signature of predetermined target gases; and continuously monitoring the amount of radiation passing through said cell.

4. The method according to claim 3 in which said step of isolating said spectral windows comprises passing said beam through a plurality of narrow bandpass optical filters.

5. The method according to claim 3 in which said plurality of narrow bandpass optical filters comprises four narrow bandpass optical filters for isolating spectral windows of at least three gases.

6. The method according to claim 5 in which said at least three gases are selected from the group consisting of $CO_2$, $H_2O$, $SF_6$, $CH_4$, $C_2H_2$, $N_2O$ and CO.

7. The method according to claim 6 including a reference channel spectrometer having a reference gas.

8. The method according to claim 6 in which said at least three gases comprise $CO_2$, $SF_6$, and $C_2H_2$.

9. The method according to claim 6 in which said at least three gases comprise $CO_2$, $CH_4$, and $N_2O$.

10. The method according to claim 6 in which said at least three gases comprise $CO_2$, $CH_4$, and CO.

11. The method according to claim 2 in which said gas mixture includes $O_2$.

12. The method according to claim 1 in which said exhaled sample from said subject is a low volume sample.

13. The method according to claim 12 in which said low volume sample is less than about 1.25 mL.

14. The method according to claim 1 in which said collimated beam is a collimated beam of IR radiation.

15. The method according to claim 14 including modulating said IR radiation at a frequency to produce a rapid response time.

16. The method according to claim 15 in which said IR radiation is modulated at a frequency greater than 50 Hz.

17. The method according to claim 16 in which said IR radiation is modulated at a frequency of approximately 2000 Hz.

18. The method according to claim 14 in which said IR radiation is combined radiation from a plurality of emitters.

19. The method according to claim 18 in which said IR radiation is combined radiation from two emitters.

20. The method according to claim 19 in which said two emitters comprise a $CO_2$ laser and a broadband thermal element.

21. The method according to claim 1 in which said sample cell is a light tube.

22. The method according to claim 1 in which said step of collecting an exhaled sample from said subject comprises filling an anesthetic bag with said sample gas mixture; connecting said anesthetic bag to a flow control valve; placing a breathing tube with said valve in the mouth of a subject; and connecting said breathing tube to said miniature sample cell.

23. The method according to claim 22 in which said flow control valve connects said subject to said container to rebreathe said mixture of gases.

24. The method according to claim 22 in which said flow control valve connects said subject to said container to inhale said mixture of gases from said container and exhale to said sample cell and ambient air.

25. The method according to claim 22 in which said sample cell is integral with said breathing tube for in situ monitoring.

26. The method according to claim 1 including filtering spectral interferences from said analyzer.

27. The method according to claim 26 in which said step of filter spectral interferences comprises inserting an optical chamber downstream from said sample cell; filling said optical chamber with a gas having the spectral interference to be removed.

28. The method according to claim 27 in which said optical cell is filled with water vapor.

29. The method according to claim 27 in which said optical cell is filled with carbon dioxide.

30. The method according to claim 1 in which said subject rebreathes said sample gas mixture.

31. The method according to claim 1 in which said subject breathes said sample gas mixture and exhales to said sample cell and ambient air.

32. The method according to claim 6 including a reference channel spectrometer.

33. A method of monitoring a subject's breath for diagnostic analysis comprising;
   delivering a sample gas mixture to a subject;
   collecting a breath sample from said subject;
   delivering said breath sample from said subject to a miniature sample cell;
   projecting collimated beams of IR radiation from a $CO_2$ laser and a broadband thermal element through said miniature sample cell;
   analyzing selected frequency components of said collimated beam with one or more spectrometers;
   storing each output from said one or more spectrometers;
   converting said outputs from each spectrometer to concentration readings;
   whereby said outputs can be processed to produce diagnostic information.

34. A method of monitoring a subject's breath for diagnostic analysis comprising;
   delivering a sample gas mixture to a subject;
   collecting a breath sample from said subject;
   delivering said breath sample from said subject to a miniature light pipe sample cell;
   projecting one or more collimated beams of radiation through said miniature sample cell;
   analyzing selected frequency components of said collimated beam with one or more spectrometers;
   storing each output from said one or more spectrometers;
   converting said outputs from each spectrometer to concentration readings;
   whereby said outputs can be processed to produce diagnostic information.

35. A method of monitoring a subject's breath for diagnostic analysis comprising;
   delivering a sample gas mixture to a subject;
   collecting a breath sample from said subject;
      said step of collecting a breath sample from said subject comprises filling an anesthetic bag with said sample gas mixture, connecting said anesthetic bag to a flow control valve, placing a breathing tube with said valve in the mouth of a subject, and connecting said breathing tube to said miniature sample cell;
   delivering said breath sample from said subject to a miniature sample cell;
   projecting one or more collimated beams of radiation through said miniature sample cell;
   analyzing selected frequency components of said collimated beam with one or more spectrometers;
   storing each output from said one or more spectrometers;
   converting said outputs from each spectrometer to concentration readings;
   whereby said outputs can be processed to produce diagnostic information.

36. The method according to claim 35 in which said flow control valve connects said subject to said container to rebreathe said mixture of gases.

37. The method according to claim 35 in which said flow control valve connects said subject to said container to inhale said mixture of gases from said container and exhale to said sample cell and ambient air.

38. The method according to claim 35 in which said sample cell is integral with said breathing tube for in situ monitoring.

39. A method of monitoring a subject's breath for diagnostic analysis comprising;
   delivering a sample gas mixture to a subject;
   collecting a breath sample from said subject;
   delivering said breath sample from said subject to a miniature sample cell;
   projecting one or more collimated beams of radiation through said miniature sample cell;
   filtering spectral interferences from said analysis by inserting an optical chamber downstream from said miniature sample cell, filling said optical chamber with a gas having the spectral interference to be filtered;
   analyzing selected frequency components of said collimated beam with one or more spectrometers;
   storing each output from said one or more spectrometers;
   converting said outputs from each spectrometer to concentration readings;
   whereby said outputs can be processed to produce diagnostic information.

40. The method according to claim 39 in which said optical cell is filled with water vapor.

41. The method according to claim 39 in which said optical cell is filled with carbon dioxide.

42. A method of monitoring a subject's breath for diagnostic analysis comprising;

delivering a sample gas mixture to a subject, said subject rebreathing said sample gas mixture;

collecting a breath sample from said subject;

delivering said breath sample from said subject to a miniature sample cell;

projecting one or more collimated beams of radiation through said miniature sample cell;

analyzing selected frequency components of said collimated beam with one or more spectrometers;

storing each output from said one or more spectrometers;

converting said outputs from each spectrometer to concentration readings;

whereby said outputs can be processed to produce diagnostic information.

* * * * *